US012582970B2

(12) United States Patent
Luo et al.

(10) Patent No.: US 12,582,970 B2
(45) Date of Patent: Mar. 24, 2026

(54) INORGANIC SOLID SILICON-BASED SULFONIC ACID AND/OR PHOSPHORIC ACID CATALYST, PREPARATION METHOD THEREFOR, AND APPLICATION THEREOF

(71) Applicant: XIANGTAN UNIVERSITY, Hunan (CN)

(72) Inventors: Hean Luo, Xiangtan (CN); Kuiyi You, Xiangtan (CN); Yibai Zeng, Xiangtan (CN); Jingbin Wen, Xiangtan (CN); Yaqing Zhang, Xiangtan (CN); Xinya Yuan, Xiangtan (CN); Qiuhong Ai, Xiangtan (CN)

(73) Assignee: XIANGTAN UNIVERSITY, Xiangtan (CN)

( * ) Notice: Subject to any disclaimer, the term of this patent is extended or adjusted under 35 U.S.C. 154(b) by 859 days.

(21) Appl. No.: 17/911,214

(22) PCT Filed: Jun. 9, 2020

(86) PCT No.: PCT/CN2020/095190
§ 371 (c)(1),
(2) Date: Sep. 13, 2022

(87) PCT Pub. No.: WO2021/176458
PCT Pub. Date: Sep. 16, 2021

(65) Prior Publication Data

US 2023/0104925 A1 Apr. 6, 2023

(30) Foreign Application Priority Data

Mar. 13, 2020 (CN) ......................... 202010177579.4

(51) Int. Cl.
*B01J 27/053* (2006.01)
*B01J 21/06* (2006.01)
(Continued)

(52) U.S. Cl.
CPC ............ *B01J 27/053* (2013.01); *B01J 21/06* (2013.01); *B01J 27/182* (2013.01); *B01J 35/37* (2024.01);
(Continued)

(58) Field of Classification Search
CPC . B01J 21/06; B01J 27/02; B01J 27/053; B01J 27/14; B01J 27/182; B01J 35/37;
(Continued)

(56) References Cited

FOREIGN PATENT DOCUMENTS

CN 105209170 A 12/2015

OTHER PUBLICATIONS

Riego, J.M., et al., 1996, Tetrahedron Letters, 37(4), 513-516. (Year: 1996).*

(Continued)

*Primary Examiner* — Brian A Mccaig
(74) *Attorney, Agent, or Firm* — RENNER KENNER GREIVE BOBAK TAYLOR & WEBER

(57) ABSTRACT

A preparation method and use of a novel pure inorganic solid silicon-based sulfonic acid and/or phosphoric acid catalytic material are disclosed. The surface hydroxyl-rich metasilicic acid is used as the raw material, and by using a sulfonating reagent and/or phosphoric acid, the sulfonic acid group and/or the phosphoric acid group are bonded to the inorganic silicon material by chemical bonding to obtain a pure inorganic solid silicon-based sulfonic acid and/or phosphoric acid catalytic material. The catalytic material can be widely used in many acid-catalyzed organic reactions such as isomerization, esterification, alkylation, hydroamination of olefins, condensation, nitration, etherification, multi-component reactions and oxidation reactions. The inorganic solid silicon-based sulfonic acid and/or phosphoric acid catalytic material of the present invention has the advantages of high acid amount, high activity, good hydrothermal
(Continued)

(1: metasilicic acid; 2: silicon-based sulfonic acid)

stability, no swelling, simple preparation, low cost, no pollution, no corrosion, easy separation and reusability.

14 Claims, 7 Drawing Sheets

(51) Int. Cl.

| | |
|---|---|
| ***B01J 27/182*** | (2006.01) |
| ***B01J 35/37*** | (2024.01) |
| ***B01J 35/61*** | (2024.01) |
| ***B01J 35/63*** | (2024.01) |
| ***B01J 35/64*** | (2024.01) |
| ***B01J 37/00*** | (2006.01) |
| ***B01J 37/02*** | (2006.01) |
| ***B01J 37/03*** | (2006.01) |
| ***B01J 37/06*** | (2006.01) |
| ***B01J 37/08*** | (2006.01) |
| ***B01J 37/20*** | (2006.01) |
| ***B01J 37/28*** | (2006.01) |
| ***B01J 37/30*** | (2006.01) |
| ***B01J 37/34*** | (2006.01) |
| ***C07D 223/10*** | (2006.01) |

(52) U.S. Cl.

CPC ........... *B01J 35/613* (2024.01); *B01J 35/615* (2024.01); *B01J 35/617* (2024.01); *B01J 35/638* (2024.01); *B01J 35/647* (2024.01); *B01J 35/651* (2024.01); *B01J 37/009* (2013.01); *B01J 37/0236* (2013.01); *B01J 37/036* (2013.01); *B01J 37/06* (2013.01); *B01J 37/08* (2013.01); *B01J 37/20* (2013.01); *B01J 37/28* (2013.01); *B01J 37/30* (2013.01); *B01J 37/343* (2013.01); *B01J 37/346* (2013.01); *C07D 223/10* (2013.01); *B01J 2235/10* (2024.01); *B01J 2235/15* (2024.01); *B01J 2235/30* (2024.01)

(58) Field of Classification Search

CPC ...... B01J 35/613; B01J 35/615; B01J 35/617; B01J 35/638; B01J 35/647; B01J 35/651; B01J 37/009; B01J 37/0236; B01J 37/036; B01J 37/06; B01J 37/08; B01J 37/20; B01J 37/28; B01J 37/30; B01J 37/343; B01J 37/346; B01J 2235/10; B01J 2235/15; B01J 2235/30; C01B 33/00; C01B 33/113

See application file for complete search history.

(56) References Cited

OTHER PUBLICATIONS

Souza et al.; Vapour phase transesterification over solid acids for the synthesis of isoamyl salicylate; Indian Journal of Chemical Technology; vol. 11, May 2004, pp. 401-409.
Jing et al.; Petrochemical Technology; Synthesis of 4,4'-Methylene Diphenyl Dimethyl Carbamate Catalyzed by Silica-Supported Sulfuric Acid; 2009, 38, 1, pp. 82-85; English abstract provided.
Elghniji et al.; Synthesis, characterization of SiO2 supported-industrial phosphoric acid catalyst for hydrolysis of NaBH4 solution.

* cited by examiner (1: metasilicic acid; 2: silicon-based sulfonic acid)

(1: metasilicic acid; 2: silicon-based sulfonic acid)

(1: metasilicic acid; 2: silicon-based sulfonic acid)

(1: metasilicic acid; 2: silicon-based sulfonic acid)

(1: metasilicic acid; 2: silicon-based sulfonic acid)

a: silicate salt; b: silicate ester; c: silica gel;

1: metasilicic acid; 2: solid silicon-based sulfonic acid catalyst material; 3: inorganic acid; 4: sulfonating reagent.

(1: silicon-based sulfonic acid powder (not baked); 2: metasilicic acid powder (not baked))

(1: baked metasilicic acid powder; 2: baked silicon-based sulfonic acid powder)

(1: silica powder; 2: metasilicic acid powder; 3: baked silicon-based sulfonic acid powder)

(1: metasilicic acid powder, 2: phosphorylated metasilicic acid powder,

3: sulfonated / phosphorylated metasilicic acid powder)

INORGANIC SOLID SILICON-BASED SULFONIC ACID AND/OR PHOSPHORIC ACID CATALYST, PREPARATION METHOD THEREFOR, AND APPLICATION THEREOF

FIELD OF THE INVENTION

The present invention relates to a pure inorganic solid silicon-based sulfonic acid and/or phosphoric acid catalytic material with high acid amount, and a preparation method and use thereof.

BACKGROUND OF THE INVENTION

According to statistics, about 85% of chemicals are produced through catalytic processes, and the development and application of a large number of catalytic materials has enabled the chemical industry to develop rapidly. In the past, the manufacturing process, activity, life and cost of new catalytic materials were researched, but some hidden factors such as the environment were rarely considered. Since the beginning of the 21st century, the combination of scientific and technological innovation and environmental protection, and the simultaneous growth and sustainable development of high enterprise efficiency and high social benefits have gradually become the goals of people, therefore, the development of green catalytic processes and environmentally friendly catalytic materials has gradually become a research hotspot. Replacing liquid acid catalysts with solid acids is one of the most important ways to achieve environmentally friendly catalytic applications. Compared with metal-organic complex catalysts, solid acid catalysts can be prepared easily, are easily separated from the reaction system after the reaction, and can be recovered and reused. In particular, some solid sulfonic acid catalysts have special structures and high acid strength and acid amount, which endow solid sulfonic acid catalysts with good activity and selectivity, making them have special properties, and are widely used in acid-catalyzed organic reactions, such as Beckmann rearrangement of ketoximes or aldoximes, esterification, alkylation, hydroamination of olefins, condensation, nitration, etherification, multi-component reactions and oxidation reactions. Therefore, the development and research of solid sulfonic acid catalytic materials to catalyze organic reactions has important academic research value and broad application prospects.

Most of the current research is on organic solid sulfonic acid catalyst materials, such as polystyrene sulfonic acid resin, perfluorosulfonic acid resin, fatty sulfonic acid strong acid cation exchange resin and so on. In the traditional preparation method, the sulfonic acid group is directly connected to the benzene ring, resulting in a poor degree of freedom of functional groups, and the reverse reaction of sulfonation of the aromatic sulfonic acid resin reduces the service life of the resin. At the same time, in many organic solvent reaction systems, this kind of sulfonic acid resin is easily swelled and broken, the sulfonic acid group is easy to detach off, and the catalyst is easy to deactivate, which limits its practical application in industry.

Another inorganic solid sulfonic acid catalytic material, such as silica gel~sulfonic acid, abbreviated as SSA, is an inorganic solid protonic acid. Generally, silica-sulfonic acid ($SiO_2$—$SO_3H$) catalysts are prepared by reacting a limited number of hydroxyl groups on the surface of silica gel with chlorosulfonic acid, by using silica gel (silica gel) with a relatively small number of surface hydroxyl groups as a raw material. This solid acid catalyst material exhibits high reactivity and good selectivity for acid-catalyzed reactions (such as condensation reaction, substitution reaction, esterification reaction, oxidation reaction, etc.). Although unwashed silica-sulfonic acid particles ($SiO_2$—$SO_3H$, referred to as silicon sulfonic acid) prepared by reacting silica gel (or silica) with a sulfonating agent have a higher acid amount, But, in practice, a large amount of acid is adsorbed on the surface of silica gel or silica, and the adsorbed acid is not covalently bonded to the silica particles. Since the number of hydroxyl groups on the surface of the silica gel is too small, the amount of sulfonic acid groups bound to the surface of the silica gel particles is limited, and the acid amount of the silica sulfonic acid particles is very low. After the silica-sulfonic acid particles ($SiO_2$—$SO_3H$) are washed with water to remove the adsorbed acid, the acid amount of the silica-sulfonic acid particles is usually less than 0.14 mmol/g, and the acid amount is difficult to reach 0.15 mmol/g, more difficult to reach 0.18 mmol/g, and almost difficult to reach 0.20 mmol/g.

U.S. Pat. No. 3,929,972A discloses the preparation of Silico-dihydrogen sulphate by sulfonation of particulate alkali metal metasilicates (eg sodium or potassium metasilicate pentahydrate) with concentrated sulfuric acid. In the early stage of the sulfonation reaction, primary sulfonated particles of soft skin-rigid core type (its acid amount is generally below 0.50 mmol/g) are formed, in which the soft skin is composed of a sol-gel composed of metasilicic acid and a small amount of silicon-based sulfonic acid ($SiO(HSO_4)_2$), and the hard core is sodium metasilicate crystals. The primary sulfonated particles are in slurry state and have low mechanical strength. As the sulfonation reaction continued, the silicon-based sulfonic acid ($SiO(HSO_4)_2$) molecules were continuously detached from the surface of the particles and entered into the sulfuric acid solution, resulting in a gradual reduction in the size of the hard core and its eventual disappearance (i.e., the basic sodium metasilicate crystal substrate is dissolved by sulfuric acid), obtaining a mixture containing the compound $SiO(HSO_4)_2$ in monomolecular form or in the form of small particles of nanometer size. The particles obtained by the baking of the primary sulfonated particles described above cannot be used as catalysts in acidic reaction systems because the basic sodium metasilicate substrate is not resistant to corrosion by acids.

In addition, in recent years, some researchers have also used alkyl-modified silicon sulfonic acid catalytic materials, such as silica gel propyl sulfonic acid, and silica gel phenyl sulfonic acid. The preparation of such catalytic materials requires the addition of a certain amount of template agents, such as cetyltrimethylammonium bromide, and silanization reagents, such as γ-mercaptopropyltrimethoxysilane, monophenyltrichlorosilane, diphenyldichlorosilane, chloropropyltrichlorosilane, octadecyltrichlorosilane, etc. It is also necessary to add a certain amount of high-cost hydrogen peroxide as an oxidant to obtain an alkyl-modified solid silicon sulfonic acid catalytic material. The preparation process of this type of catalytic material is complicated, the cost is high, and its structure still contains an alkyl chain, and it has a certain swelling property in organic reactions, which makes its sulfonic acid group unstable and easy to detach off and inactivate.

SUMMARY OF THE INVENTION

The purpose of the present invention is to provide pure inorganic solid silicon-based sulfonic acid and/or phosphoric acid catalytic material and its preparation method. The method comprises using a metasilicic acid solid with a surface rich in hydroxyl groups as a starting material, bonding the sulfonic acid group and/or the phosphoric acid group to the inorganic silicon material in the form of chemical bonding by a sulfonating agent and/or a phosphorylating agent, thereby obtaining a pure inorganic solid silicon-based sulfonic acid/phosphoric acid catalytic material (h-SSA) with high acid amount, i.e., solid silico-sulfonic acid and/or -phosphoric acid.

The inventors of the present application have unexpectedly found that, by using a sulfonating agent and/or a phosphorylating agent to sulfonate and/or phosphorylate a metasilicic acid solid with a surface rich in hydroxyl groups, not only granular sulfonated and/or phosphorylated metasilicic acid solids with high acid amount is obtained, but also the structure and particle shape of the granular metasilicic acid solid particles is not destroyed, and the size of the metasilicic acid particles is hardly or not changed. Then, by further drying and baking, solid silicon-based sulfonic acid and/or phosphoric acid particles or powders with high acid amount and high mechanical strength are obtained. If the sulfonated and/or phosphorylated metasilicic acid particles are only dried at a higher temperature (eg above 200° C.) without baking, then it is possible that the metasilicic acid substrate inside the particles is converted to a silica gel substrate (which contains water), but the solid sulfonic acid and/or phosphoric acid particles comprising the silica gel substrate still have a high acid amount.

In the present application, the inorganic solid silicon-based sulfonic acid and/or phosphoric acid catalyst (h-SSA) may be referred to as a (inorganic) solid acid catalyst or a (inorganic) solid siliceous acid with high acid amount (solid silico-acid with high surface-acidity, referred to as h-SSA).

In the present application, AG is an abbreviation for acid group. In addition, silico-sulfonic acid and silico-sulfuric acid are equivalent concepts, and the two are used interchangeably. The silico-acid component includes silico-sulfonic acid and/or -phosphoric acid catalyst, or silicon-based sulfonic acid and/or phosphoric acid catalyst.

According to a first embodiment of the present invention, the present invention provides an inorganic solid silicon-based sulfonic acid and/or phosphoric acid catalyst (h-SSA), the solid acid catalyst (h-SSA) comprises:

a substrate component (A): a silicon-containing substrate without sulfonic acid group(s) and/or phosphoric acid group(s); and a silicon-based acid component (B): an inorganic silicon-based sulfonic acid and/or—phosphoric acid containing (covalently linked) sulfonic acid group(s) and/or phosphoric acid group(s), i.e., an inorganic silico-oxide compounds having

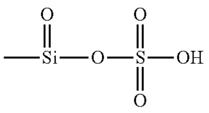

and/or

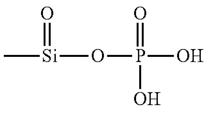

groups;

wherein, the substrate component (A) in the above-mentioned silicon-based sulfonic acid and/or phosphoric acid catalyst (h-SSA) includes or is selected from one or two or three of the following silicon-containing substrate components: (1) metasilicic acid (ie, a transparent glassy solid); (2) silica gel, and (3) silica (SiO2).

The solid acid catalyst (h-SSA) is in particulate (or granular) form or powder form. The silicon-based acid component (B) is located on the surface of the catalyst particles, and the silicon substrate component (A) is located inside the catalyst particles.

As inorganic silicon-based sulfonic acid and/or phosphoric acid containing a sulfonic acid group(s) and/or a phosphoric acid group(s), the silicon-based acid component (B) includes a compound having the general formula (I), a compound having the general formula (II) and a compound of general formula (III); or the silicon-based acid component (B) is one or more selected from the group consisting of a compound of the general formula (I), a compound of the general formula (II) and a compound of the general formula (III); or the silicon-based acid component (B) is (mainly) composed of one or more of a compound of the general formula (I), a compound of the general formula (II) and a compound of the general formula (III):

(I)

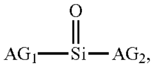

(II)

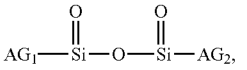

and (III)

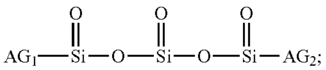

wherein, $-AG_1$ and $-AG_2$ are each independently $—O—SO_3H$, $—O—PO_3H_2$ or —OH, and $-AG_1$ and $-AG_2$ are not both —OH. Preferably, $-AG_1$ and $-AG_2$ are each independently $—O—SO_3H$ or —OH, or $—O—PO_3H_2$ or —OH, and $-AG_1$ and $-AG_2$ are not both —OH.

In this application, silicon-containing substrate has the same meaning as silicon substrate or siliceous substrate or Si substrate.

The acid amount of the solid acid catalyst (h-SSA) (hydrogen ion molar amount per catalyst mass) is 0.25-8.4 mmol/g, preferably 0.3-8.2, preferably 0.35-8, preferably 0.4-7.8, preferably 0.5-7.6, preferably 0.6-7.5, preferably 0.7-7.3, preferably 0.8-7.0, preferably 0.9-6.8, preferably 1.0-6.5, preferably 1.1-6.3, preferably 1.2-6.0, preferably 1.3-5.8, preferably 1.4-5.6, preferably 1.5-5.4, preferably 1.6-5.2, preferably 1.8-5.3, preferably 2.0-5.1, preferably 2.2-5.0, preferably 2.4-4.8, eg 3 or 4 mmol/g.

The average particle size of the solid acid catalyst (h-SSA) is 1 μm-10 mm, preferably 3 μm-5 mm, preferably 5 μm-1 mm, preferably 7-800 μm, preferably 10-750 μm, more preferably 15-700 μm, more preferably 20-650 μm, more preferably 25-600 μm, more preferably 30-550 μm, more preferably 35-500 μm, more preferably 40-450 μm, more preferably 45-400 μm, more preferably 50-350 μm, more preferably 55-320 μm, such as 60, 70, 80, 90, 100, 110, 120, 130, 150, 170, 180, 190, 200, 220, 240, 260, 280, or 300 μm. If the particle size of the catalyst is too small, it is not convenient to filtration recovery and reuse. In addition, in some continuous reactions, if the particle size of the solid acid catalyst is too small (such as nano-sized particle size), it will block the outlet and pipes of the reactor, increase the pressure in the reactor, and cause an explosion accident. Preferably, its average particle size is greater than 40 μm or 50 μm or 60 μm.

In the present application, the solid metasilicic acid and/or phosphoric acid powder or granules as starting materials have the same or similar average particle size as the solid silicon-based sulfonic acid and/or phosphoric acid catalyst product (h-SSA).

The acid amount refers to: molar amount of hydrogen ions/per unit mass of inorganic solid silicon-based sulfonic acid and/or phosphoric acid catalyst (h-SSA).

Preferably, the acid amount of the solid acid catalyst (h-SSA) is 1.0-7.2 mmol/g, preferably 1.3-6.8, preferably 2.0-6.5, preferably 2.1-6.3, preferably 2.2-6.0, preferably 2.3-5.8, preferably 2.4-5.6, preferably 2.5-5.4, preferably 2.6-5.2, preferably 2.7-5.3, preferably 2.8-5.1, preferably 2.9-5.0, preferably 3.0-4.8, for example 3.4, 3.6, 4 or 4.4 mmol/g, and the average particle size of the solid acid catalyst (h-SSA) is 20-600 μm, preferably 35-550 μm, preferably 40-500 μm, preferably 45-450 μm, preferably 50-400 μm, preferably 55-320 μm, preferably 60-320 μm, e.g. 70, 80, 90, 100, 110, 120, 130, 150, 170, 180, 190, 200, 220, 240, 260, 280 or 300 μm.

More preferably, the average particle size of the solid acid catalyst (h-SSA) is 50-400 μm, more preferably 55-350 μm, such as 60, 70, 80, 90, 100, 110, 120, 130, 150, 180, 200, 230, 250, 280 or 300 μm, and its acid amount is 1.0-6.5 mmol/g, preferably 1.1-6.3, preferably 1.2-6.0, preferably 1.3-5.8, preferably 1.4-5.6, preferably 1.5-5.4, preferably 1.6-5.2, preferably 1.8-5.3, preferably 2.0-5.1, preferably 2.2-5.0, preferably 2.4-4.8 mmol/g, eg 3 or 4 mmol/g.

Preferably, when the substrate component (A) is a metasilicic acid solid (ie, a transparent glassy solid) and/or silica gel, the acid amount of the solid acid catalyst (h-SSA) is 0.25-7.6 mmol/g, preferably 0.3-7.5, more preferably 0.35-7.4, more preferably 0.4-7.2, more preferably 0.45-7.0, preferably 0.5-6.8, preferably 0.55-6.6, preferably 0.6-6.2, preferably 0.65-5.8, preferably 0.7-5.4, preferably 0.75-5.0, preferably 0.8-4.8 mmol/g.

Preferably, when the substrate component (A) is a silica substrate, the acid amount of the solid acid catalyst (h-SSA) is 0.25-8.2 mmol/g, preferably 0.3-8.0 mmol/g, preferably 0.35-7.8 mmol/g g, more preferably 0.4-7.6 mmol/g, more preferably 0.45-7.4 mmol/g, more preferably 0.5-7.2 mmol/g, preferably 0.55-7.0, preferably 0.6-6.8, preferably 0.65-6.6, preferably 0.7-6.2, preferably 0.75-5.8, preferably 0.8-5.4, preferably 0.85-5.2, preferably 0.9-5.0 mmol/g.

When the substrate component (A) in the granular catalyst (h-SSA) comprises or is a silica substrate, the solid acid catalyst (h-SSA) is obtained from sulfonated and/or phosphorylated metasilicic acid particles by baking; more preferably, it is obtained by drying and baking of the sulfonated and/or phosphorylated metasilicic acid particles.

Generally, the sum of the weights of (A) and (B) is 80-100 wt %, preferably 83-100 wt %, preferably 85-100 wt %, preferably 87-100 wt %, preferably 90-100 wt %, such as 93, 95, 97 or 98 or 99 wt %, based on the total weight of the catalyst (h-SSA). It is also possible that the particulate catalyst (h-SSA) also comprises small amounts (eg, 0-20 wt %, 0-15 wt %, 0-10 wt %, 0-5 wt % or 1-3 wt %) of other substances or impurities other than (A) and (B).

Preferably, the weight ratio of the silicon-based acid component (B) to the substrate component (A) is: 0.02-20:1, preferably 0.04-18:1, preferably 0.08-15:1, preferably 0.15-12:1, preferably 0.2-10:1, preferably 0.25-9.5:1, preferably 0.3-9:1, preferably 0.35-8.5:1, preferably 0.4-8:1, preferably 0.5-7.5:1, preferably 0.6-7:1, e.g. 0.8:1, 0.9:1, 1:1, 1.2:1, 1.5:1, 2:1, 2.5:1, 3:1, 3.5:1, 4:1, 4.5:1, 5:1, 5.5:1, 6:1, 6.5:1.

Preferably, the silicon-based acid component (B) comprises:

- 60-100 wt % (preferably 63-100 wt %, preferably 65-100 wt %, preferably 68-100 wt %, preferably 70-100 wt %, preferably 75-100 wt %, preferably 80-100 wt %, such as 85, 90, 95 or 98 wt %) of a compound of the general formula (I);
- 0-40 wt % (preferably 0-37 wt %, preferably 0-35 wt %, preferably 0-32 wt %, preferably 0-30 wt %, preferably 0-25 wt %, preferably 0-20 wt %, such as 15, 10, 5 or 2 wt %) of a compound of the general formula (II); and
- 0-30 wt % (preferably 0-27 wt %, preferably 0-25 wt %, preferably 0-22 wt %, preferably 0-20 wt %, preferably 0-15 wt %, preferably 0-10 wt %, such as 8, 5 or 2 wt %) of a compound of the general formula (III);
- wherein the weight percent is based on the total weight of the silicon-based acid component (B).

Preferably, the sum of the weights of the compound of the general formula (I), the compound of the general formula (II) and the compound of the general formula (III) is 80-100 wt %, preferably 83-100 wt %, preferably 85-100 wt %, preferably 87-100 wt %, preferably 90-100 wt %, such as 93, 95, 97 or 98 or 99 wt %, based on the total weight of the silicon-based acid component (B). It is also possible that the silicon-based acid component (B) also comprises small amounts (eg, 0-20 wt %, 0-15 wt %, 0-10 wt %, 0-5 wt % or 1-3 wt %) of polysilicic acid components and/or impurities other than compounds of the general formula (I), (II) and (III).

Preferably, the molar ratio of the compound of the general formula (I), the compound of the general formula (II) and the compound of the general formula (III) is 1:(0-0.7):(0-0.3), preferably 1:(0.01-0.6):(0-0.25), preferably 1:(0.05-0.55):(0-0.20), preferably 1:(0.08-0.5):(0-0.17), preferably 1:(0.1-0.45):(0.002-0.15), Preferably 1:(0.12-0.4):(0.005-0.10).

The crushing strength of the solid acid catalyst particles (h-SSA) of the present invention is greater than 60N, preferably 60-260N, preferably 70-250N, preferably 80-240N, preferably 90-230N, such as 100N, 110N, 120N, 130N, 140N, 150N, 160N, 165N, 170N, 173N, 175N or 180N.

More specifically, the metasilicic acid substrate is dry metasilicic acid solid, the silica gel substrate is dry silica gel, or, preferably, the silica substrate is amorphous silica (ie, baked silica). Preferably, the crushing strength of the baked solid acid catalyst (h-SSA) particles is greater than 165N, preferably in the range of 165-260N, more preferably in the range of 170-260N, preferably 173-250N, preferably 175-240N or 178-230N or 180-230N.

In general, substrate component (A) may be a mixture or combination of any two or three of the above-mentioned substrates (1), (2) and (3). In addition, the silica substrate may contain a small amount (eg, 0-20 wt %, preferably 0-10 wt %, preferably 1-5 wt %) of impurities (eg, silica gel).

The acid amount stated here refers to the amount of acids measured for the covalently bonded sulfonic acid groups and/or phosphoric acid groups in the solid acid catalyst (h-SSA or h-SSA-1), that is, the solid acid catalyst (h-SSA or h-SSA-1) contains no or almost no adsorbed sulfonating agent (sulfuric acid or chlorosulfonic acid) and/or phosphorylating agent (phosphoric acid).

In the present application, a (dry) metasilicic acid substrate refers to a silicon substrate comprising 80-100 wt %

(preferably 85-100 wt %, preferably 90-100 wt %, such as 92 or 95 or 97 or 99 wt %) metasilicic acid. The metasilicic acid substrate may also contain impurities, such as sodium metasilicate; preferably, the content of alkali metals (such as sodium and potassium) in the metasilicic acid substrate is 0-300 ppm, preferably 0-200 ppm, preferably 0-100 ppm, preferably 0-50 ppm, preferably 0-10 ppm.

In addition, the silica substrate in the (baked) solid acid catalyst particles refers to a silicon substrate comprising 80-100 wt % (preferably 85-100 wt %, preferably 90-100 wt %, such as 92 or 95 or 97 or 99 wt %) of amorphous silica, such that the crushing strength of the silicon substrate is higher than 170N, eg 170-240N. The silica substrate may also contain small amounts of impurities, such as silica gel. In addition, the silica gel substrate may also contain small amounts of impurities, such as metasilicic acid. Preferably, the content of alkali metals (eg sodium and potassium) in the silica substrate is 0-300 ppm, preferably 0-200 ppm, preferably 0-100 ppm, preferably 0-50 ppm, preferably 0-10 ppm.

Dried metasilicic acid refers to the metasilicic acid solid dried at a temperature of room temperature (20° C.)~150° C. (preferably 60~120° C., more preferably 70-90° C.), preferably, drying is under reduced pressure or under vacuum. It should be pointed out that when the drying temperature is higher (eg 120-150° C.), the drying time should be reduced (eg, generally 0.5-6 hours, such as 0.5-2 hours) to prevent most of the metasilicic acid from being converted into silica gel.

Baked silica refers to the silica substrate formed from the metasilicic acid substrate after the dried sulfonated/phosphorylated metasilicic acid particles being baked at a temperature above 120° C. (eg 120-600° C., preferably 150-500° C., more preferably 200-480° C.), preferably, the baking is carried in an inert atmosphere. The silica substrate in the baked solid acid catalyst has higher strength (eg crush strength or abrasion resistance).

In the present application, the silicon-based sulfonic acid and/or phosphoric acid catalyst is also referred to as silico-sulfonic acid and/or silico-phosphoric acid catalyst. Silicon-based sulfonic acid and/or phosphoric acid means the following three species: silicon-based sulfonic acid, silicon-based phosphoric acid, and silicon-based sulfonic acid+phosphoric acid.

In the present application, as the substrate component (A), the silicon-containing substrate without sulfonic acid group and/or phosphoric acid group refers to the silicon-containing substrate without sulfonic acid group (or sulfuric acid group) and phosphoric acid group.

The compound of the general formula (I) includes or is one or more of the following compounds:

(Ia)

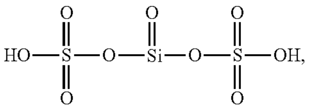

(Ib)

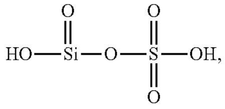

(Ic)

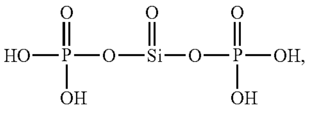

-continued (Id)

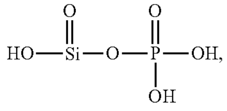

and (Ie)

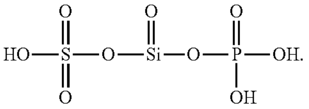

The compound of the general formula (II) is monocondensates of the compound of the general formula (I). The compound of the general formula (II) includes or is one or more of the following compounds:

(IIa)

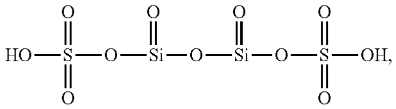

(IIb)

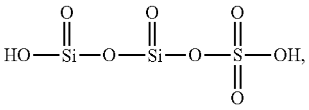

(IIc)

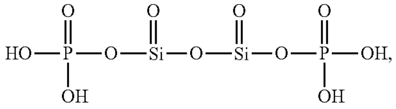

(IId)

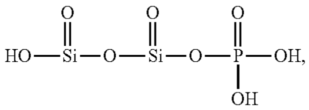

and (IIe)

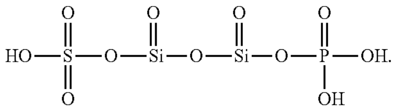

The compound of the general formula (III) is a dicondensate of the compound of the general formula (I). The compound of the general formula (III) includes or is one or more of the following diacid compounds and monoacid compounds:

(IIIa)

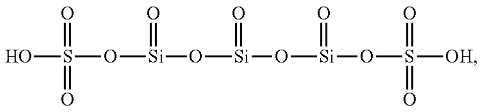

(IIIb)

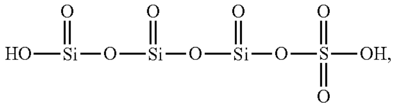

(IIIc)

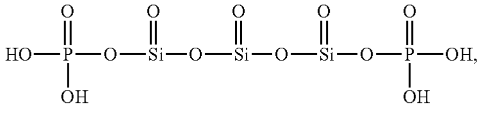

-continued (IIId)

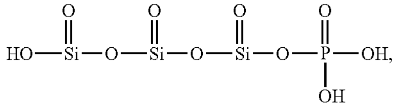

and (IIIe)

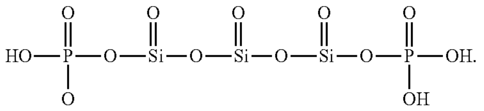

In the present application, as the silicon-based acid component (B), when $-AG_1$ and $-AG_2$ are each independently $—O—SO_3H$ or —OH, and $-AG_1$ and $-AG_2$ are not both —OH, the silicon-based sulfonic acid compound includes or is the compound of the general formulae (Ia), (Ib), (Ha), (IIb), (Ma) and (Mb). When $-AG_1$ and $-AG_2$ are each independently $—O—PO_3H_2$ or —OH, and $-AG_1$ and $-AG_2$ are not both —OH, the silicon-based phosphoric acid compound includes or is the compound of the general formulae (Ic), (Id), (IIc), (IId), (Mc) and (IIId). Silicon-based sulfonic acid/phosphoric acid compound includes or is the compound of the general formulae (Ie), (IIe), and (IIIe). When both the sulfonating agent and the phosphorylating agent are used, the silicon-based component (B) of the resulting solid acid catalyst (h-SSA) includes all compounds of the general formulae (I), (II) and (III).

The baked granular catalyst (h-SSA) is rubbed in the palm of the hand, it was clearly felt that it had a sandy touch and the particles were hard.

The BET surface area of the solid acid catalyst (h-SSA) is 50-800 $m^2/g$, preferably 100-600 $m^2/g$, preferably 150-500 $cm^2/g$, preferably 200-400 $m^2/g$.

Usually, the pore volume of the solid acid catalyst (h-SSA) is 50-700 $cm^3/g$, preferably 100-600 $cm^3/g$, preferably 130-550 $cm^3/g$, preferably 150-500 $cm^3/g$, preferably 160-400 $cm^3/g$, preferably 180-300 $cm^3/g$.

Typically, the solid acid catalyst (h-SSA) has an average pore diameter of 4-100 nm, preferably 5-50 nm, more preferably 6-30 nm, more preferably 7-20 nm, more preferably 8-13 nm.

Preferably, the solid acid catalyst (h-SSA) of the present invention is prepared by the following process:

subjecting a silicon source to an ion exchange reaction or a hydrolysis reaction with an inorganic acid (preferably, the pH of the reaction mixture is controlled to be 4.5-6.5 during the reaction, preferably 5-6), to obtain orthosilicic acid ($H_4SiO_4$) gel or sol;

allowing the orthosilicic acid gel or sol to stand for crystallization (promoting structural reorganization) to obtain a solution containing granular orthosilicic acid ($H_4SiO_4$) gel, filtering the solution and washing the resulting filter cake with water until the filtrate is neutral, and drying (more preferably, vacuum drying) the separated gel to obtain dry granular or powdered metasilicic acid ($H_2SiO_3$) raw material;

sulfonating and/or phosphorylating the dried granular metasilicic acid ($H_2SiO_3$) raw material with a sulfonating agent and/or a phosphorylating agent, filtering the resulting reaction mixture and washing the resulting filter cake with water or an organic solvent until the filtrate is neutral, and then drying (preferably vacuum-drying) the separated granular sulfonated and/or phosphorylated solid to obtain dry inorganic solid acid powder (that is, solid acid particles in which the silicon substrate is metasilicon acid);

finally, baking the inorganic solid acid powder to obtain a solid acid catalyst (h-SSA) (ie, solid acid particles in which the silicon substrate is silica).

Additionally, the present invention provides an inorganic solid silicon-based sulfonic acids (ie, a solid silicon-based sulfonic acid catalyst h-SSA-1) which comprise or essentially comprise one or more of the following inorganic silicon-based sulfonic acids of formula (I) below, or which consist (mainly) of one or more of the following inorganic silicon sulfonic acids of formula (I):

(I)

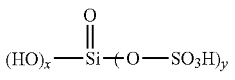

in the formula, x=0 or 1, y=1 or 2, x+y=2.

Specifically, the inorganic solid silicon-based sulfonic acid of the present invention (ie, the solid silicon-based sulfonic acid catalyst h-SSA-1) comprises or mainly comprises inorganic silicon sulfonic acid of the following formula (Ia) and/or (Ib), or comprises or mainly comprises one or both of the inorganic silicon sulfonic acids of formula (Ia) and (Ib) below, or consists (mainly) of inorganic silicon sulfonic acids of formula (Ia) and/or (Ib) below, or consists (mainly) of one or both of the inorganic silicon sulfonic acids of the following formulae (Ia) and (Ib):

(Ia)

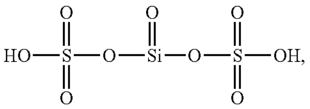

(Ib)

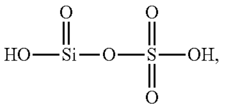

In addition, the inorganic solid silicon-based sulfonic acid of the present invention (ie, the solid silicon-based sulfonic acid catalyst h-SSA-1) comprises or mainly comprises the inorganic silicon-based sulfonic acids of formula (Ia) and/or (Ib) and optionally non-sulfonated metasilicic acid (also called silicic acid) or silicon dioxide (since metasilicic acid becomes silicon dioxide after baking), or consists mainly of inorganic silicon sulfonic acids of formula (Ia) and/or (Ib) and optionally unsulfonated metasilicic acid or silica. The content of unsulfonated metasilicic acid or silica may be 0 wt %.

"Optional" means with or without the subsequent component(s). The molecular weight of the inorganic silicon sulfonic acid compound of the chemical formula (Ia) is 238, and the molecular weight of the inorganic silicon sulfonic acid compound of the chemical formula (Ib) is 158.

Typically, the inorganic solid silicon-based sulfonic acid of the present invention (ie, the solid silicon-based sulfonic acid catalyst h-SSA-1) is in particulate form or in powder form. Typically, it also comprises unsulfonated metasilicic acid ($H_2SiO_3$) or silica ($SiO_2$) within the particles.

In the present application, preferably, the inorganic solid silicon-based sulfonic acid (ie, the solid silicon-based sulfonic acid catalyst h-SSA-1) has an average particle size of 10 nm to 10 mm. Preferably, the average particle size is 50 nm-5 mm, preferably 80 nm-1000 μm, more preferably 150 nm-800 μm, more preferably 250 nm-600 μm, more preferably 450 nm-500 μm, more preferably 600 nm-300 μm, more preferably 800 nm-250 μm, more preferably 1 μm-200 μm, more preferably 10 μm-170 μm, more preferably 20 μm-150 μm, such as 30, 40, 50, 60, 70, 80, 90, 100, 110, 120 or 130 μm. In the present application, the solid metasilicic acid (powder or granular) as the starting material has the same or similar average particle size as the solid silicon-based sulfonic acid catalyst product (h-SSA-1).

Preferably, the acid amount (hydrogen ion molar amount per catalyst mass) of the inorganic solid silicon-based sulfonic acid (ie, the solid silicon-based sulfonic acid catalyst h-SSA-1) is 0.05-8.4 mmol/g, preferably 0.7-8.2 mmol/g, preferably 0.1-8 mmol/g, preferably 0.3-7.8, preferably 0.5-7.6, preferably 0.6-7.5, preferably 0.7-7.3, preferably 0.8-7.0, preferably 0.9-6.8, preferably 1.0-6.5, preferably 1.1-6.3, preferably 1.2-6.0, preferably 1.3-5.8, preferably 1.4-5.6, preferably 1.5-5.4, preferably 1.6-5.2, preferably 1.8-5.3, preferably 2.0-5.1, preferably 2.2-5.0, preferably 2.4-4.8 mmol/g, for example 3 or 4 mmol/g. For example, the acid amount of the catalyst is 0.1-8 mmol/g, more preferably 0.3-7.8, more preferably 0.5-7.5, more preferably 0.7-7.0, preferably 0.8-6.5 mmol/g, more preferably 1-6.0 mmol/g.

The acid amount refers to: the molar amount of hydrogen ions/per unit mass of the inorganic solid silicon-based sulfonic acid (or solid silicon-based sulfonic acid catalyst h-SSA-1).

Preferably, the average particle size of the inorganic solid silicon-based sulfonic acid (ie, the solid silicon-based sulfonic acid catalyst h-SSA-1) is 10 μm-170 μm, more preferably 20 μm-150 μm, such as 30, 40, 50, 60 μm, 70, 80, 90, 100, 110, 120 or 130 μm, and its acid amount is 1.0-6.5 mmol/g, preferably 1.1-6.3, preferably 1.2-6.0, preferably 1.3-5.8, preferably 1.4-5.6, preferably 1.5-5.4, preferably 1.6-5.2, preferably 1.8-5.3, preferably 2.0-5.1, preferably 2.2-5.0, preferably 2.4-4.8 mmol/g, eg 3 or 4 mmol/g.

When the solid particulate metasilicic acid is sulfonated with a sulfonating agent to obtain an inorganic solid silicon-based sulfonic acid (ie, the solid silicon-based sulfonic acid catalyst h-SSA-1), since there will be part of the metasilicic acid is not sulfonated during the reaction, therefore, the obtained inorganic solid silicon-based sulfonic acid (ie, the solid silicon-based sulfonic acid catalyst h-SSA-1) comprises the two inorganic silicon-based sulfonic acids of the above-mentioned chemical formulae (Ia) and (Ib) and unsulfonated metasilicic acid ($H_2SiO_3$), or consists of the three compounds, or mainly consists of the three compounds.

Preferably, the inorganic solid silicon-based sulfonic acid of the present invention (ie, the solid silicon-based sulfonic acid catalyst h-SSA-1) comprises 1-100 wt % (preferably 2-96 wt %, more preferably 4-92 wt %, more preferably 6-88 wt %, more preferably 8-84 wt %, more preferably 10-80 wt %, more preferably 15-75 wt %, more preferably 20-70 wt %, more preferably 25-65 wt %, more preferably 30-60 wt %, such as 40 wt %) of the inorganic silicon sulfonic acid of the above-mentioned chemical formula (Ia) and/or (Ib) and 0-99 wt % (preferably 4-98 wt %, more preferably 8-96 wt %, more preferably 12-94 wt %, more preferably 16-92 wt %, more preferably 20-90 wt %, more preferably 25-85 wt %, more preferably 30-80 wt %, more preferably 35-75 wt %, more preferably 40-70 wt %, eg 60 wt %) of unsulfonated metasilicic acid or silicon dioxide, the percentage is based on the weight of the inorganic solid silicon-based sulfonic acid (catalyst h-SSA-1). It is also possible that it also comprises small amounts (eg, 0-45 wt % or 0-30 wt % or 0-20 wt % or 0-10 wt %) of other substances or impurities or doping substances.

Preferably, the inorganic solid silicon-based sulfonic acid (h-SSA-1) of the present invention comprises 0.5-90 wt % (preferably 1-85 wt %, preferably 2-80 wt %, preferably 3-75 wt %, preferably 4-70 wt %, preferably 5-65 wt %, for example 15, 20, 30, 35, 40, 42, 44, 46, 48, 50, 55 wt % or 60 wt %) of the inorganic silicon sulfonic acid of formula (Ia) above, 0.5-90 wt % (preferably 1-85 wt %, preferably 2-80 wt %, preferably 3-75 wt %, preferably 4-70 wt %, preferably 5-65 wt %, eg 15, 20, 30, 35, 40, 42, 44, 46, 48, 50, 55 wt % % or 60 wt %) of the inorganic silicon sulfonic acid of the above chemical formula (Ib) and 0-99 wt % (preferably 4-98 wt %, more preferably 8-96 wt %, more preferably 12-94 wt %, more preferably 16-92 wt %, more preferably 20-90 wt %, more preferably 25-85 wt %, more preferably 30-80 wt %, more preferably 35-75 wt %, more preferably 40-70 wt %, eg 50 wt %, 60 wt %) of unsulfonated metasilicic acid (or silica). The percentage is based on the weight of the inorganic solid silicon-based sulfonic acid (catalyst h-SSA-1).

Surprisingly, when the acid amount of the inorganic solid silicon-based sulfonic acid (ie, the solid silicon-based sulfonic acid catalyst h-SSA-1) is 0.05 or 0.1 mmol, the content of the two inorganic silicon sulfonic acids of the formula (Ia) and/or (Ib) in the inorganic solid silicon-based sulfonic acid (catalyst h-SSA-1) is about 0.6 wt % or 1.2 wt %, and the catalyst is acidic enough to have a good catalytic effect. When the acid amount of the inorganic solid silicon-based sulfonic acid (ie, the solid silicon-based sulfonic acid catalyst h-SSA-1) is 6 mmol, the content of the two inorganic silicon-based sulfonic acids of the formula (Ia) and/or (Ib) in the solid silicon-based sulfonic acid (catalyst) is about 71-95 wt %, eg 83, 85, 88 wt %. In the catalyst, the balance is unsulfonated metasilicic acid (or silica) and impurities or other doping species.

Theoretically, for a solid particulate (eg, solid spherical) inorganic solid silicon-based sulfonic acid (ie, the solid silicon-based sulfonic acid catalyst h-SSA-1), a large number of sulfonic acid groups are present on the surface of the particles group. When its particle size (or particle size) is larger, its acid amount is lower. However, for porous inorganic solid silicon-based sulfonic acid (i.e., solid silicon-based sulfonic acid catalyst h-SSA-1), its specific surface area is significantly increased, and therefore, it is also possible for the catalyst particles with larger particle diameters to have higher acid amount.

Typically, the two inorganic silicon-based sulfonic acid compounds and the unsulfonated metasilicic acid or silica are distributed in the inorganic solid silicon-based sulfonic acid (ie, solid silicon-based sulfonic acid catalyst h-SSA-1) particles, thus, the amount of sulfonic acid of the solid silicon-based sulfonic acid catalyst depends on the degree of sulfonation of the metasilicic acid.

The specific surface area of the inorganic solid silicon-based sulfonic acid (ie, the solid silicon-based sulfonic acid catalyst h-SSA-1) is 50-800 $m^2/g$, preferably 100-600 $m^2/g$, preferably 150-500 $cm^2/g$, preferably 200-400 $m^2/g$.

Typically, the pore volume of the inorganic solid silicon-based sulfonic acid (ie, the solid silicon-based sulfonic acid catalyst h-SSA-1) is 100-600 $cm^3/g$, preferably 130-550 $cm^3/g$, preferably 150-500 $cm^3/g$, preferably 160-400 $cm^3/g$.

The average pore diameter of the inorganic solid silicon-based sulfonic acid (ie, the solid silicon-based sulfonic acid catalyst h-SSA-1) is 4-100 nm, preferably 5-50 nm, more preferably 6-30 nm, more preferably 7-20 nm, more preferably 8-13 nm.

The solid acid catalyst of the present invention (ie, h-SSA-1, baked) has a crush strength greater than 165N, preferably 165-260N, 170-250N, 173-240N, 175-230N or 180-230N.

According to the second embodiment of the present invention, the present invention also provides a method for preparing the above-mentioned inorganic solid silicon-based sulfonic acid and/or phosphoric acid catalyst (h-SSA), the method comprising:

(B) sulfonation and/or phosphorylation of metasilicic acid: the (dried) granular metasilicic acid ($H_2SiO_3$) raw material is reacted with a sulfonating agent and/or a phosphorylating agent, the resulting reaction product is separated (preferably, filtered to separate out the cake) and washed with water or organic solvent (preferably, the filter cake is washed with water until the filtrate is neutral), and then dried to obtain dry inorganic solid silicon-based sulfonic acid and/or phosphoric acid particles (i.e., sulfonated and/or phosphorylated metasilicic acid powder or granules). That is, a dried but unbaked inorganic solid silicon-based sulfonic acid and/or phosphoric acid catalyst (h-SSA) in which the silicon-containing substrate is a metasilicic acid solid is obtained.

The amount of the sulfonating agent and/or phosphorylating agent relative to metasilicic acid is sufficient to make the acid amount of the dried but unbaked solid acid catalyst (h-SSA) to be 0.25-7.6 mmol/g, preferably 0.3-7.5, more preferably 0.35-7.4, more preferably 0.4-7.2, more preferably 0.45-7.0, preferably 0.5-6.8, preferably 0.55-6.6, preferably 0.6-6.2, preferably 0.65-5.8, preferably 0.7-5.4, preferably 0.75-5.0, preferably 0.8-4.8 mmol/g.

In addition, the present invention also provides a method for preparing the above-mentioned inorganic solid silicon-based sulfonic acid catalyst (h-SSA-1), the method comprising:

(B) sulfonation: the granular metasilicic acid ($H_2SiO_3$) raw material is reacted with the sulfonating agent, the resulting reaction product is separated (preferably, filtering and separating out the filter cake) to obtain the sulfonated metasilicic acid solid of the present invention (ie, wet solid of inorganic solid silicon sulfonic acid). Then, the filter cake is washed with water or an organic solvent (preferably with water until the washing liquid is neutral), and dried (preferably under vacuum). Dry inorganic solid silicon-based sulfonic acid particles (ie, powder or particles of sulfonated metasilicic acid) are obtained. That is, a dried but unbaked inorganic solid silicon-based sulfonic acid catalyst (h-SSA-1) in which the silicon-containing substrate is a metasilicic acid solid was obtained.

The amount of the sulfonating agent relative to the metasilicic acid is sufficient to make the acid amount of the dried but unbaked solid acid catalyst (h-SSA-1) to be 0.25-7.6 mmol/g, preferably 0.3-7.5, more preferably 0.35-7.4, more preferably 0.4-7.2, more preferably 0.45-7.0, preferably 0.5-6.8, preferably 0.55-6.6, preferably 0.6-6.2, preferably 0.65-5.8, preferably 0.7-5.4, preferably 0.75-5.0, preferably 0.8-4.8.

In the above two preparation methods of the present invention, preferably, the raw material of granular metasilicic acid (H2SiO3) is obtained by crystallization of orthosilicic acid gel, and the crystal structure and pore structure of the obtained (undried or dried) metasilicic acid solid are improved and its specific surface area is significantly increased. Therefore, metasilicic acid solid is a mesoporous material.

Therefore, in the present application, particulate metasilicic acid (H2SiO3) raw material refers to particulate metasilicic acid solids.

Additionally, the obtained sulfonated metasilicic acid wet solids or silicon-based sulfonic acid and/or phosphoric acid wet solids can be used directly as catalysts in certain reactions. Preferably, the sulfonated metasilicic acid wet solid or the silicon-based sulfonic acid and/or phosphoric acid wet solid is further dried or vacuum dried to obtain a dry sulfonated metasilicic acid solid (which is in powder or granular form) or a dry silicon-based sulfonic acid and/or phosphoric acid solids (in powder or granular form).

In the present application, the sulfonating agent is one or more selected from the sulfonating agents: oleum, sulfuric acid (preferably, concentrated sulfuric acid; preferably, concentrated sulfuric acid with a concentration of 65-100 wt %, for example: concentrated sulfuric acid with a concentration or mass fraction of 70-100 wt % or 75-100 wt %; such as 95-99 wt % concentrated sulfuric acid), chlorosulfonic acid, sulfur trioxide, sulfuryl chloride, a mixture of sulfur dioxide and chlorine, a mixture of sulfur dioxide and oxygen, a mixture of sulfur dioxide and ozone, sulfamic acid, and sulfite; more preferably, the sulfonating agent is one or more of oleum, concentrated sulfuric acid (preferably, concentrated sulfuric acid in which the concentration or mass fraction is 70-100 wt % or 75-100 wt %), chlorosulfonic acid or sulfur trioxide.

The phosphorylating agent is phosphoric acid, phosphoryl monochloride and/or phosphoryl dichloride, preferably concentrated phosphoric acid, such as concentrated phosphoric acid at a concentration of 75 wt %-85 wt %.

The metasilicic acid ($H_2SiO_3$) raw material is a powdered or granular solid (ie dry solid or wet solid). The solid metasilicic acid raw material is a porous metasilicic acid or a metasilicic acid with pores or a foamed metasilicic acid.

Here, metasilicic acid is also called silicic acid.

Preferably, the obtained dry granular silicon-based sulfonic acid and/or phosphoric acid solid is baked in order to increase the strength of the particles, thereby obtaining a baked silicon-based sulfonic acid and/or phosphoric acid solid (which is in powder or granular form), that is, the catalyst h-SSA in which the silicon substrate is silica.

Preferably, the resulting sulfonated metasilicic acid wet solid or the obtained dried sulfonated metasilicic acid solid is baked to obtain the baked sulfonated metasilicic acid solid (which is in the form of powder or particulate matter), i.e., the catalyst h-SSA-1.

In the above-mentioned method for preparing silicon-based sulfonic acid and/or phosphoric acid, preferably, the method further comprises the following step:

(C) baking: the dry granular silicon-based sulfonic acid and/or phosphoric acid (solid powder) obtained in step (B) is baked to obtain an inorganic solid silicon-based sulfonic acid and/or phosphoric acid catalyst (that is, baked silicon-based sulfonic acid and/or phosphoric acid solid h-SSA, which is generally in powder or granular form). That is, the solid acid catalyst h-SSA in which the silicon-containing substrate is silica was obtained.

In the above-described method for preparing silicon-based sulfonic acid, preferably, the method further comprises the following step:

(C) baking: the sulfonated metasilicic acid solid obtained in step (B) is baked to obtain the inorganic solid silicon-based sulfonic acid of the present invention (that is, the baked sulfonated metasilicic acid solid h-SSA-1, it is generally in powder or granular form).

The acid amount of the baked solid acid catalyst (h-SSA, or h-SSA-1) is 0.25-8.4 mmol/g, preferably 0.3-8.4 mmol/g, preferably 0.32-8.4 mmol/g, preferably 0.33-8.4 mmol/g g, preferably 0.35-8.2 mmol/g, preferably 0.36-8.0 mmol/g, preferably 0.38-7.8 mmol/g, preferably 0.38-7.6 mmol/g, more preferably 0.4-7.6 mmol/g, more preferably 0.45-7.4 mmol/g g, more preferably 0.5-7.2 mmol/g, preferably 0.55-7.0, preferably 0.6-6.8, preferably 0.65-6.6, preferably 0.7-6.2, preferably 0.75-5.8, preferably 0.8-5.4, preferably 0.85-5.2, preferably 0.9-5.0.

In the above-mentioned two preparation methods, preferably, the method further comprises the following step:

(A) preparation of granular metasilicic acid $H_2SiO_3$ raw material: the ion exchange reaction or hydrolysis reaction of a silicon source and an inorganic acid (preferably, in the reaction, the pH value of the reaction mixture is controlled at 4.5-6.5, preferably 5-6) is carried out to obtain orthosilicic acid ($H_4SiO_4$) gel or sol; the orthosilicic acid gel or sol is allowed to stand and crystallize (promoting structural reorganization) to obtain a solution containing particulate orthosilicic acid ($H_4SiO_4$) gel, then the solution is filtered and the resulting filter cake is washed with water until the filtrate is neutral, and the separated gel is dried (more preferably, vacuum dried) to obtain dry granular or powdery metasilicic acid ($H_2SiO_3$) raw material. It is then used in step (B) above.

Preferably, in the above-described method for preparing silicon-based sulfonic acid, the method further comprises the following step:

(A) preparation of metasilicic acid $H_2SiO_3$ raw material: ion exchange reaction or hydrolysis reaction of a silicon source and an inorganic acid is carried out to obtain orthosilicic acid ($H_4SiO_4$) gel (ie, silicon-containing solution); orthosilicic acid gel is crystallized, to obtain a solution containing orthosilicic acid ($H_4SiO_4$) gel, then the gel is separated from the solution and dried (ie, solid-liquid separation, solid washing and drying) to obtain metasilicic acid ($H_2SiO_3$) raw material (powdered or granular solid).

In the above-mentioned two preparation methods, the following preferred conditions can also be used:

Crystallization refers to crystallization by standing. Orthosilicic acid gels are less stable and form metasilicic acid solids upon drying.

Metasilicic acid is prepared by using a liquid phase precipitation method.

The silicon source in the step (A) is one or more of silicate salt, silicate ester or silica gel. wherein the cation of the silicate is one or more of metal ions (eg, alkali metal ions, such as potassium or sodium ions) or ammonium ions. The silicate ester is tetra-$C_1$-$C_{15}$ hydrocarbyl orthosilicate, preferably tetra-$C_1$-$C_{10}$ hydrocarbyl orthosilicate. The silicate ester is tetra-$C_1$-$C_7$ alkyl orthosilicate, tetra-$C_3$-$C_8$ cycloalkyl orthosilicate or tetraaryl orthosilicate, such as tetramethyl orthosilicate, tetraethylorthosilicate, tetrapropyl orthosilicate, tetrabutyl orthosilicate and tetraphenyl orthosilicate.

The inorganic acid used in the step (A) is one or more of hydrochloric acid, sulfuric acid, nitric acid and phosphoric acid.

Preferably, the above step (B) or step (A) is carried out under stirring or under the action of stirring plus ultrasonic waves or microwaves, so as to obtain particles with uniform particle size. In step (A), the concentration of orthosilicic acid in the orthosilicic acid gel solution formed, and the temperature and time of crystallization determine the particle size of the particulate metasilicic acid solid.

Preferably, the above-mentioned step (B) is carried out as follows: sulfonation is carried out by adding a sulfonating agent, or a sulfonating agent and/or a phosphorylating agent, to the metasilicic acid under stirring conditions or under the action of stirring plus ultrasonic waves or microwaves; then the sulfonated metasilicic acid is cooled (for example, cooled to room temperature) and filtered, the obtained filter cake is washed with deionized water until the filtrate becomes neutral, and the obtained white solid powder is dried (for example, vacuum dried) and baked to obtain inorganic solid silicon based sulfonic acid catalytic material, or inorganic solid silicon-based sulfonic acid and/or phosphoric acid catalytic material.

Preferably, in step (B), the molar ratio of the metasilicic acid to the sulfonating agent, or the molar ratio of the metasilicic acid to the sulfonating agent and/or phosphorylating agent, is 0.01~4.0:1, preferably 0.03~3.0:1, preferably 0.04~2.0:1, preferably 0.05~1:1, more preferably 0.1~0.9:1, more preferably 0.2~0.8:1, more preferably 0.3~0.7:1. The temperature of the sulfonation reaction is from room temperature (20° C.) to 200° C., preferably 40 to 180° C., preferably 60 to 150° C., more preferably 80 to 130° C.

Preferably, in step (B), the drying of the solid powder can be carried out under air or an inert gas atmosphere; more preferably at a pressure of 5 to 150 kPa, preferably 10 to 120 kPa (absolute pressure); the drying temperature is from room temperature (20° C.) to 150° C., preferably 60 to 120° C.

In the step (C), the solid baking is carried out under an inert gas atmosphere; preferably, the baking temperature is 120-600° C., preferably 150-500° C., more preferably 200-480° C.

Preferably, the above-mentioned step (A) is carried out as follows: under stirring or under the action of stirring plus ultrasonic waves or microwaves, an inorganic acid solution is slowly added dropwise to a solution containing the silicon source (to carry out ion exchange reaction or hydrolysis reaction); the pH value of the solution is maintained (for example, at 4.5~6.5, preferably 5~6) to obtain orthosilicic acid ($H_4SiO_4$) gel (wet gel or gel solution); and then this gel (for example, at a temperature from room temperature to 80° C.) is crystallized by standing, filtered, and washed (for example, with water) until the filtrate is neutral (pH=7), and finally the obtained gel is dried (for example, vacuum-dried) to obtain solid granular or powdered metasilicic acid ($H_2SiO_3$).

Further, in the step (A), the ion exchange or hydrolysis is carried out under stirring or under the action of stirring plus ultrasonic waves or microwaves. The molar ratio of the silicon source material (silicate salt or silicate ester or silica gel) to the inorganic acid is 0.01~2.0:1, preferably 0.05~1.0:1, more preferably 0.1~0.8:1, more preferably 0.3~0.7:1, for example, 0.05~0.7:1, preferably 0.1~0.65:1, preferably 0.15~0.6:1, preferably 0.2~0.5:1. The temperature of ion exchange or hydrolysis is 0 to 100° C., preferably room temperature (20° C.) to 80° C.

Further, in the step (A), the crystallization conditions of the orthosilicic acid gel are: the pH value of the gel solution is 1-9, preferably 2-7; the crystallization temperature is 0-100° C., preferably 10-90° C., more preferably from room temperature (20° C.) to 80° C., more preferably 30° C. to 70° C. In the step (A), the drying of the gel solid (ie, the gel solid after washing) is carried out under air or an inert gas atmosphere. Preferably, the drying of the orthosilicic acid gel solid is carried out under a pressure (absolute pressure) of 5 to 150 kPa, preferably 10 to 120 kPa. The drying temperature is from room temperature (20° C.) to 200° C., preferably 60 to 150° C., and more preferably 60 to 110° C. When the orthosilicic acid gel is dried at a higher temperature (eg 150-200° C.), the drying time should be shortened accordingly, eg to 10 minutes-4 hours, in order to avoid the formation of silica gel.

The drying of the orthosilicic acid gel, especially under vacuum, is to form particulate metasilicic acid solids and to completely remove moisture from the metasilicic acid solid particles. The sulfonated and/or phosphorylated solid particles are firstly dried and then baked, which is beneficial to obtain a solid acid catalyst (h-SSA or h-SSA-1) with stable structure and high strength. Preferably, the sulfonated and/or phosphorylated solid particles are dried in an inert atmosphere and then baked in an inert atmosphere, forming a pure silica substrate in the interior of the particles.

Of course, if the orthosilicic acid gel is dried at higher temperatures (eg above 200° C., eg 200-400° C.) and the resulting sulfonated and/or phosphorylated solid particles are not baked, it is possible that a silica gel substrate is formed in the interior of the particles. In this case, the silicon substrate of the catalyst of the present invention is silica gel. Although this solid acid catalyst comprising a silica gel substrate also has a high acid amount, it is not the preferred technical solution of the present invention.

The present invention also provides a method of preparing an inorganic solid sulfonic acid and/or phosphoric acid catalyst (h-SSA), comprising: subjecting a silicon source to an ion exchange reaction or a hydrolysis reaction with an inorganic acid (preferably, controlling the pH value of the reaction mixture during the reaction to be 4.5-6.5, preferably 5~6) to obtain orthosilicic acid ($H_4SiO_4$) gel or sol; standing the orthosilicic acid gel or sol for crystallization (promoting structural reorganization), thereby obtaining a solution containing granular orthosilicic acid ($H_4SiO_4$) gel; filtering the solution, and washing the resulting filter cake with water until the filtrate is neutral; drying the separated gel (more preferably, vacuum drying) to obtain a dry granular or powdery metasilicic acid ($H_2SiO_3$) raw material; sulfonating and/or phosphorylating the dried granular metasilicic acid ($H_2SiO_3$) raw material with a sulfonating agent and/or a phosphorylating agent, and filtering the resulting reaction mixture and washing the resulting filter cake with water or an organic solvent until the filtrate is neutral, and drying the isolated particulate sulfonated and/or phosphorylated solid (preferably in a vacuum) to obtain a dry inorganic solid acid powder (i.e., solid acid particles in which the silicon substrate is metasilicic acid); finally, baking the inorganic solid acid powder to obtain a solid acid catalyst (h-SSA) (that is, the solid acid particles in which the silicon substrate is silica).

The present invention provides inorganic solid silicon-based sulfonic acid and/or phosphoric acid (ie, solid silicon-based sulfonic acid and/or phosphoric acid catalyst h-SSA) or inorganic solid silicon-based sulfonic acid (ie, solid silicon-based sulfonic acid catalyst h-SSA-1) prepared by the above method. The inorganic solid silicon-based sulfonic acid and/or phosphoric acid catalyst (h-SSA), or, the inorganic solid silicon-based sulfonic acid catalyst h-SSA-1 (or catalytic material), can also be a supported catalyst or catalytic material. Preferably, the carrier of the supported inorganic solid silicon-based sulfonic acid and/or phosphoric acid catalyst or the supported inorganic solid silicon-based sulfonic acid catalyst is one or more selected from the carriers such as molecular sieves, γ-alumina, activated carbon, silica gel, and clay which having a higher specific surface area.

Preferably, the molecular sieve is MCM-41, MCM-22, SBA-15, HZSM-5, mordenite, Y-type zeolite or beta zeolite.

The present invention also provides the use of the above-mentioned inorganic solid silicon-based sulfonic acid and/or phosphoric acid catalyst (h-SSA) or the above-mentioned inorganic solid silicon-based sulfonic acid (h-SSA-1) as a catalyst. In particular, it is used in many acid-catalyzed organic reactions such as isomerization reactions, esterification reactions, alkylation reactions, hydroamination reactions of olefins, condensation reactions, nitration reactions, etherification reactions, amination reactions of alcohols (for example, for the amination of ethylene glycol to prepare ethylenediamine), preparation of β-enaminone, multi-component reactions and oxidation reactions.

By comparing the FT-IR spectra (FIG. 1) of both silicic acid (ie metasilicic acid) and the inorganic solid silicon-based sulfonic acid of the present invention (ie, solid silicon-based sulfonic acid catalyst), it can be found that a new characteristic infrared absorption peak appears around 1394 $cm^{-1}$ in the infrared spectrum of the silicon-based sulfonic acid, the peak is attributed to the stretching vibration of O═S═O. In addition, compared with the intensity of the infrared characteristic signal peak at 1101 $cm^{-1}$ of metasilicic acid, the intensity of the infrared characteristic signal peak at 1101 $cm^{-1}$ of silicon-based sulfonic acid is also significantly increased, which is due to the fact that it is caused by the coincidence of the infrared characteristic absorption peak of O—S—O in the sulfonic acid group and the asymmetric stretching vibration signal peak of the Si—O—Si in the catalyst framework main-body.

At the same time, it can be seen from FIG. 3 that the metasilicic acid sample has no obvious infrared absorption peak in the wavelength range of 1400 to 1640 $cm^{-1}$. After sulfonation, the inorganic solid silicon-based sulfonic acid catalyst showed four distinct infrared characteristic absorption peaks in the wavelength range of 1400-1640 $cm^{-1}$. The infrared absorption peaks located at 1454 $cm^{-1}$ and 1622 $cm^{-1}$ are the characteristic absorption peaks of pyridine adsorbed on the Lewis acid center; the infrared absorption peak at 1546 $cm^{-1}$ is the characteristic absorption peak of pyridine adsorbed on the Bronsted acid center, which is mainly provided by the $—SO_3H$ group; and the infrared absorption peak at 1491 $cm^{-1}$ is the characteristic absorption peak produced by the simultaneous adsorption of pyridine on Lewis acid and Bronsted acid centers. Obviously, the acid component (B) in the silicon-based sulfonic acid catalyst includes a major amount of the compound of the general formula (I) and a small amount of the silicon-based sulfonic acid compound of the general formula (II).

Advantages of the Present Invention

The inorganic solid silicon-based sulfonic acid and/or phosphoric acid catalyst or the inorganic solid silicon-based sulfonic acid catalyst of the present invention has the advantages of high acid amount, high activity, good hydrothermal stability, no swelling, simple preparation, low cost, no pollution, no corrosion, easy separation, reusability and the like, thus it is an environmentally friendly solid acid catalytic material with broad application prospects. The catalytic material can be widely used in many acid-catalyzed organic reactions such as isomerization, esterification, alkylation, hydroamination of olefins, condensation, nitration, etherification, multi-component reactions and oxidation reactions. For example, solid acid catalysts used in the esterification of gallic acid with C1-C8 fatty alcohols can achieve high yields of 96-99% in the reversible reaction, which may be attributed to the steric hindrance effect of the catalyst particles, which makes the reverse reaction of water attacking the ester product hardly occurs.

In particular, by crystallization of orthosilicic acid gel, granular metasilicic acid solids in which the crystal structure and pore structure are improved and the specific surface area are significantly increased are obtained. The particulate metasilicic acid solids before and after drying, as well as the final silicon-based sulfonic acid particles, are mesoporous materials. These materials have high mechanical strength, for example, its crush strength is greater than 60N (preferably, 60-260N, 80-250N, 100-240N, such as 120N, 150N, 160N, 165N, 170N, 175N or 180N), thus its wear resistance is significantly improved. The solid acid catalyst of the present invention contains no adsorbed sulfonic or phosphoric acid. It is used continuously for the reaction in the fluidized bed reactor, for example, for more than 400 hours, and its acid amount remains unchanged.

In particular, the solid acid catalyst of the present invention is resistant to corrosion by strong acids.

The sulfonated granular product is dried to remove moisture and then baked. This can prevent the catalyst particles from cracking during baking, thereby helping to maintain the structure and size of the catalyst particles.

DETAILED DESCRIPTION OF THE INVENTION

Figure 1:
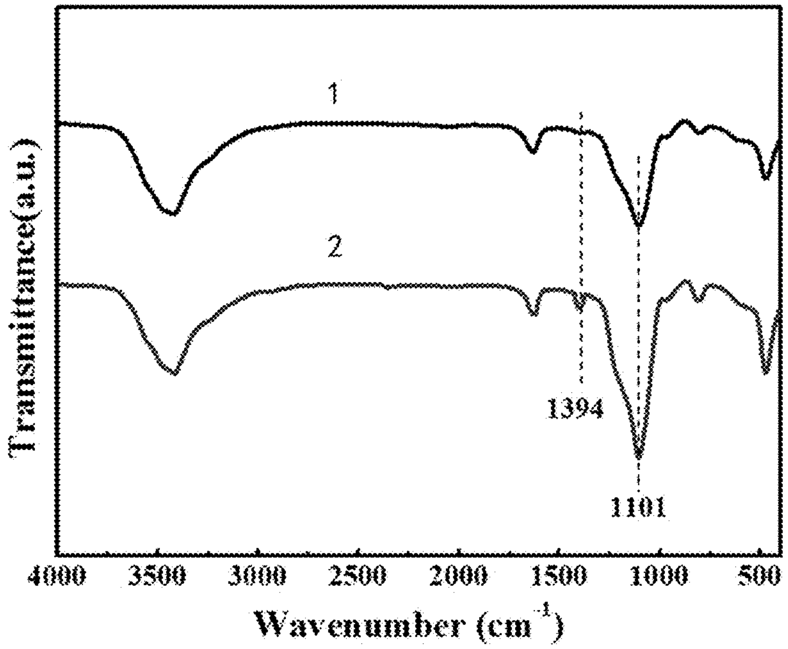
FIG. 1 is a FT-IR chart of infrared characterization of the inorganic solid silicon-based sulfonic acid catalyst of Example 1 of the present invention. 1: metasilicic acid; 2: silicon-based sulfonic acid.

The following examples describe preparation methods and uses of inorganic solid silico-sulfonic acid catalytic materials (catalysts for short), but the present invention is not limited to these examples.

1. Method of Measuring Acid Amount of Particulate Silicon-Based Sulfonic Acid Catalyst Weigh approximately 0.5 g (accurate to 0.0001) of the vacuum dried solid silico-sulfonic acid catalyst (not containing adsorbed sulfonic acid and/or phosphoric acid), add to a 250 mL Erlenmeyer flask, then add 25 mL of a freshly prepared saturated NaCl solution, shake the Erlenmeyer flask well, seal the mouth of the Erlenmeyer flask with plastic wrap, and then shake well every 4 h, after ion exchange for 24 h, add 2~3 drops of phenolphthalein indicator and titrate the amount of acid with 0.1 mol/L NaOH standard solution. For each solid acid, titrate in parallel at least 3 times with relative error control within 1%. Record the volume of NaOH consumed, calculate the amount of acid in mmol H+/g according to the formula below.

$$\text{acid amount} = \frac{C_{NaOH} \times V_{NaOH}}{m}.$$

2. Method of Measuring Crush Strength

According to the China National Standard GB/T 3780.16-1983 method, determine crush strength of solid acid catalyst particles, using Model DL5 smart particle strength meter.

Measurement procedure: measuring the particle size of the prepared sample granules individually and then placing the sample granules on sample platform of Model DL5 smart particle strength meter, applying force to break them, recording applied load at which granules crush, and determining their crush strength results.

Example 1

50 g of sodium silicate nonahydrate was thoroughly dissolved in 400 mL of deionized water, so as to obtain sodium silicate solution. Then 200 mL of 1.8 mol/L hydrochloric acid solution was added to the sodium silicate solution (molar ratio of sodium silicate to hydrochloric acid was 0.5), an ion exchange reaction was performed at room temperature, controlling pH to 5~6, and orthosilicic acid ($H_4SiO_4$) gel was obtained. The resulting gel was then crystallized by standing at 60° C. for 12 hours, re-filtered, and washed with water, until the filtrate was neutral. Finally the obtained gel solid was dried under vacuum at 110° C. for 12 h, obtaining solid powder metasilicic acid ($H_2SiO_3$), the specific surface area thereof was measured to be 293 $m^2$/g.

5 g of metasilicic acid powder with an average particle size of 90 μm was added to 100 mL of concentrated sulfuric acid (concentration 98 wt %), stirred, and sulfonated at 130° C. for 6 h, then cooled to room temperature, filtered, and the filter cake was washed with deionized water until the filtrate was neutral, the resulting white solid powder (wet solid) was dried under vacuum at 110° C. for 5 h, the dried inorganic solid silicon-based sulfonic acid powder (crush strength 105 N) was obtained. Finally, the dried sulfonated solid powder was baked under nitrogen atmosphere for 3 h at 200° C., resulting in inorganic solid silicon-based sulfonic acid catalytic material (baked inorganic solid silicon-based sulfonic acid) (crush strength 185 N) having an acid amount of 3.419 mmol/g and a BET specific surface area of 286 $m^2/g$. Structural characterization of the catalytic material was shown in FIGS. 1-5.

Example 2

280 mL of a 1.8 mol/L hydrochloric acid solution was dropped into 21 g of an ethanol solution of tetraethyl orthosilicate (0.1 mol) (molar ratio of silicate to hydrochloric acid was 0.2), the hydrolysis reaction was carried out at 20° C., controlling pH to 5~6, and orthosilicic acid ($H_4SiO_4$) gel was obtained. This gel was then crystallized by standing at 60° C. for 12 hours, re-filtered and washed, until the filtrate was neutral. Finally the obtained gel solid was dried under vacuum at 110° C. for 12 h, obtaining solid powder metasilicic acid ($H_2SiO_3$), the specific surface area thereof was measured to be 305 $m^2/g$. 5 g of metasilicic acid powder with an average particle size of 88 μm was added to 100 mL of concentrated sulfuric acid, stirred, and sulfonated at 130° C. for 6 h, then cooled to room temperature, filtered, and the filter cake was washed with deionized water until the filtrate was neutral, the obtained white solid powder was dried under vacuum at 110° C. for 5 h, and finally the dried sulfonated solid powder was baked under nitrogen atmosphere at 200° C. for 3 h to obtain an inorganic solid silicon-based sulfonic acid catalytic material having an acid amount of 3.532 mmol/g and a BET specific surface area of 295 $m^2/g$.

Comparative Example 1

Silica gel sulfonic acid catalytic material was prepared using a silica gel by a direct sulfonation method. 5 g of 90 μm of silica gel was added to 100 mL of concentrated sulfuric acid for direct sulfonation, stirred, and sulfonated at 130° C. for 6 h, then cooled to room temperature, filtered, and the filter cake was washed with deionized water until the filtrate was neutral; the resulting white solid powder was dried under vacuum at 110° C. for 5 h and finally the dried sulfonated solid powder was baked under nitrogen atmosphere for 3 h at 200° C. to obtain an inorganic solid silica gel sulfonic acid catalytic material having a measured acid amount of only 0.133 mmol/g, a BET specific surface area of 185 $m^2/g$, an average particle size of 85 μm and a crush strength of 165 N.

Example 3 (Application Example—Catalyst Stability)

Stability investigation of inorganic solid silicon-based sulfonic acid catalytic material. The inorganic solid silicon-based sulfonic acid catalytic material of Example 1 described herein was selected for cyclohexanone oxime liquid phase Beckmann rearrangement system, the service life thereof was investigated, the catalytic material was operated at a reaction temperature of 130° C. for 136 h, there was no significant drop in cyclohexanone oxime conversion and caprolactam selectivity, with cyclohexanone oxime conversion maintained at 98% and caprolactam selectivity maintained at 99%, and little drop in acid amount measured after the reaction.

Comparative Example 2 (Application Example—Catalyst Stability)

Stability investigation of organic-type solid sulfonic acid catalytic material. Commercial sulfonic acid resin of type 742B was selected for cyclohexanone oxime liquid phase Beckmann rearrangement system. The results showed that, after the catalyst was operated at 130° C. for 12 hours, the catalyst substantially lost activity, and the catalyst swelled significantly in the reaction solution, the structure thereof was compromised, and had a significant drop in acid amount, the acid amount drops to only 0.05 mmol/g.

Example 4

The experimental procedure was as in Example 1, except that microwave field was added during ion exchange reaction, and resulting inorganic solid silicon-based sulfonic acid catalytic material was measured to have acid amount of 4.215 mmol/g. The silicon-based sulfonic acid particles had average particle size of 103 μm and crush strength of 198 N.

Example 5

The experimental procedure was as in Example 1, except that microwave field was added during metasilicic acid sulfonation, and resulting inorganic solid silicon-based sulfonic acid catalytic material was measured to have acid amount of 4.932 mmol/g. The particles had average particle size of 96 μm and crush strength of 201 N.

Example 6

The preparation procedure was as in Example 1, except that molar ratio of sodium silicate nonahydrate to hydrochloric acid was 1.0, and resulting inorganic solid silicon-based sulfonic acid catalytic material with acid amount of 2.986 mmol/g. The particles had average particle size of 101 μm and crush strength of 195 N.

Example 7

The preparation procedure was as in Example 2, except that molar ratio of silicate ester to hydrochloric acid was 1.0, and resulting inorganic solid silicon-based sulfonic acid catalytic material with acid amount of 3.215 mmol/g. The particles had average particle size of 97 μm and crush strength of 209 N.

Example 8

The preparation procedure was as in Example 2, except that temperature of ion exchange reaction was 60° C., and resulting inorganic solid silicon-based sulfonic acid catalytic material with acid amount of 3.053 mmol/g. The particles had average particle size of 96 μm and crush strength 198 N.

Example 9

The preparation procedure was as in Example 2, except that temperature of hydrolysis reaction was 50° C., and resulting inorganic solid silicon-based sulfonic acid catalytic material with acid amount of 3.648 mmol/g. The particles had average particle size of 102 μm and crush strength of 188 N.

Example 10

The preparation procedure was as in Example 1, except that inorganic acid used was nitric acid, and resulting inorganic solid silicon-based sulfonic acid catalytic material with acid amount of 3.421 mmol/g. The particles had average particle size of 99 μm and crush strength of 185 N.

Example 11

The preparation procedure was as in Example 1, except that metasilicic acid sulfonation reagent was chlorosulfonic acid, and resulting inorganic solid silicon-based sulfonic acid catalytic material with acid amount of 3.515 mmol/g. The particles had average particle size of 84 μm and crush strength of 179 N.

Example 12

The preparation procedure was as in Example 1, except that metasilicic acid sulfonation reagent was sulfur trioxide, and resulting inorganic solid silicon-based sulfonic acid catalytic material with acid amount of 3.815 mmol/g. The particles had average particle size of 78 μm and crush strength of 168 N.

Example 13

The preparation procedure was as in Example 1, except that pH of gel solution was maintained at 8, and resulting inorganic solid silicon-based sulfonic acid catalytic material with acid amount of 2.056 mmol/g. The particles had average particle size of 88 μm and crush strength of 205 N.

Example 14

The preparation procedure was as in Example 1, except that temperature of gel crystallization was 80° C., and resulting inorganic solid silicon-based sulfonic acid catalytic material with acid amount of 1.988 mmol/g. The particles had average particle size of 92 μm and crush strength 187 N.

Example 15

The preparation procedure was as in Example 1, except that gel drying temperature was changed to 120° C., and resulting inorganic solid silicon-based sulfonic acid catalytic material with acid amount of 1.885 mmol/g. The particles had average particle size of 99 μm and crush strength of 194 N.

Example 16

The preparation procedure was as in Example 1, except that metasilicic acid was sulfonated at temperature of 100° C., and resulting inorganic solid silicon-based sulfonic acid catalytic material with acid amount of 2.568 mmol/g. The baked catalyst particles had average particle size of 108 μm and crush strength 198 N.

Example 17

The preparation procedure was as in Example 1, except that metasilicic acid was sulfonated at temperature of 140° C., and resulting inorganic solid silicon-based sulfonic acid catalytic material with acid amount of 3.058 mmol/g. The particles had average particle size of 95 μm and crush strength of 191 N.

Example 18

The preparation procedure was as in Example 1, except that solid silicon-based sulfonic acid catalytic material was dried at temperature of 90° C., and resulting inorganic solid silicon-based sulfonic acid catalytic material with acid amount of 3.357 mmol/g. The particles had average particle size of 96 μm and crush strength of 188 N.

Example 19 (Application Example)

The inorganic solid silicon-based sulfonic acid catalytic material of Example 1 according to the present invention can also be used in other acid catalyzed reactions, such as isomerization, hydroamination, alkylation, multi-component, esterification, etherification, nitration, oxidation, addition reaction and the like, with superior results as shown in Table 1.

TABLE 1

Catalytic Reaction Results of Inorganic Solid Silicon-based sulfonic Acid Catalytic Material

| Reaction type | Reaction raw material | Reaction Conditions | Conversion rate (%) | Target Product Selectivity (%) |
|---|---|---|---|---|
| Isomerization reaction | Ethylbenzene | Temperature 150° C., time 4 h | 90.2 | Xylene: 99.5 |
| Isomerization reaction | Cyclohexanone oxime | Temperature 130° C., time 4 h | 98.7 | Caprolactam 99.0 |
| Hydroamination reaction | Cyclohexene + cyclohexylamine | Temperature 260° C., dwell time 13.5 seconds | 95.5 | Dicyclohexylamine: 98.9 |
| Alkylation reaction | Phenol + Methanol | Temperature 200° C., time 6 h | 90.8 | P-Methylphenol: 85.8 |
| Esterification | Pyrogallic acid + ethanol | Temperature 120° C., time 2 h | 96.5 | Ethyl pyrogallate: 99.5 |

TABLE 1-continued

Catalytic Reaction Results of Inorganic Solid Silicon-based sulfonic Acid Catalytic Material

| Reaction type | Reaction raw material | Reaction Conditions | Conversion rate (%) | Target Product Selectivity (%) |
|---|---|---|---|---|
| Multicomponent reaction | Aldehydes, amines and trimethylsilanitrile | Temperature 80° C., time 3 h | 91.4 | 2,3-dihydroquinazoline: 96.8 |
| Etherification | Ethanol | Temperature 140° C., time 5 h | 88.5 | Diethyl ether: 98.7 |
| Nitration | Toluene + $NO_2$ | Oxygen aeration, temperature 30° C., time 2 h | 93.7 | P-Nitrotoluene: 90.5 |
| Oxidation reaction | Dihydropyridine + sodium nitrite | Temperature 160° C., time 7 h | 98.6 | Pyridine: 97.8 |
| Oxidation reaction | Benzyl alcohol + molecular oxygen | Temperature 150° C., time 2 h | 85.9 | Benzaldehyde: 96.9 |
| Addition reaction | Cyclohexene + methanol | Temperature 130° C., time 4 h | 95.6 | Cyclohexyl methylether: 98.7 |

Example 20—Preparation of Inorganic Solid Silico-Phosphoric Acid Catalyst 3 g of solid metasilicic acid powder (average particle size 90 μm) was added in a 50 mL two-necked round bottom flask with a stir bar, mounting the round bottom flask on an iron stand, 30 mL phosphoric acid (concentration 85 wt %) was added with a constant pressure funnel, a thermometer was inserted below the liquid level, the another port of the flask was connected to a condensing and refluxing device, the flask was sealed, placed in a thermostatic magnetic stirrer, refluxing at 100° C. for 4 h. After completion of the reaction, the solution and catalyst in the round bottom flask were poured into a sand core funnel to suction filtration, then washed with distilled water until the last drop of filtrate was neutral. The upper catalyst was taken out, and then put into a vacuum drying oven at 110° C. for 12 hours, phosphorylated inorganic solid metasilicic acid powder was obtained (FT-IR spectrum thereof was shown in FIG. 13, curve 2). Finally, the dried solid powder was baked under nitrogen atmosphere for 3 h, the baking temperature was 200° C., and resulting inorganic solid silicon-based phosphoric acid catalyst was measured to have acid amount of 2.885 mmol/g, a specific surface area of 268 $m^2$/g, an average particle size of about 89.7 μm, and a crush strength of 185 N. For elemental analysis of the catalyst, the content of alkali metals (e.g., sodium and potassium) was below the detection limit (below 3 ppm), and the content of alkaline earth metals (e.g., calcium and magnesium) was below the detection limit.

Example 21—Preparation of Inorganic Solid Silicon-Based Sulfonic Acid/Phosphoric Acid Catalyst 3 g of solid metasilicic acid powder (average particle size 90 μm) was added in a 50 mL two-necked round bottom flask with a stir bar, mounting the round bottom flask on an iron stand, 15 mL phosphoric acid (concentration 85 wt %), 15 mL concentrated sulfuric acid (concentration 98 wt %) were added sequentially with a constant pressure funnel, a thermometer was inserted below the liquid level, the other port of the flask was connected to a condensing and refluxing unit, the flask was sealed, placed in a thermostatic magnetic stirrer, refluxing at 100° C. for 4 h. After completion of the reaction, the solution and catalyst in the round bottom flask were poured into a sand core funnel to suction filtration, then washed with distilled water until the last drop of filtrate was neutral. The upper catalyst was taken out, and then put into a vacuum drying oven at 110° C. for 12 hours, sulfonated/phosphorylated inorganic solid metasilicic acid powder was obtained (FT-IR spectrum thereof was shown in FIG. 13, curve 3). Finally, the dried solid powder was baked under nitrogen atmosphere for 3 h, the baking temperature was 200° C., and resulting inorganic solid silicon-based sulfonic acid/phosphoric acid catalyst was measured to have acid amount of 3.685 mmol/g, a specific surface area of 305 $m^2$/g, an average particle size of about 89.3 μm, and a crush strength of 186 N. For elemental analysis of the catalyst, the content of alkali metals (e.g., sodium and potassium) was below the detection limit, and the content of alkaline earth metals (e.g., calcium and magnesium) was also below the detection limit.

Figure 13:
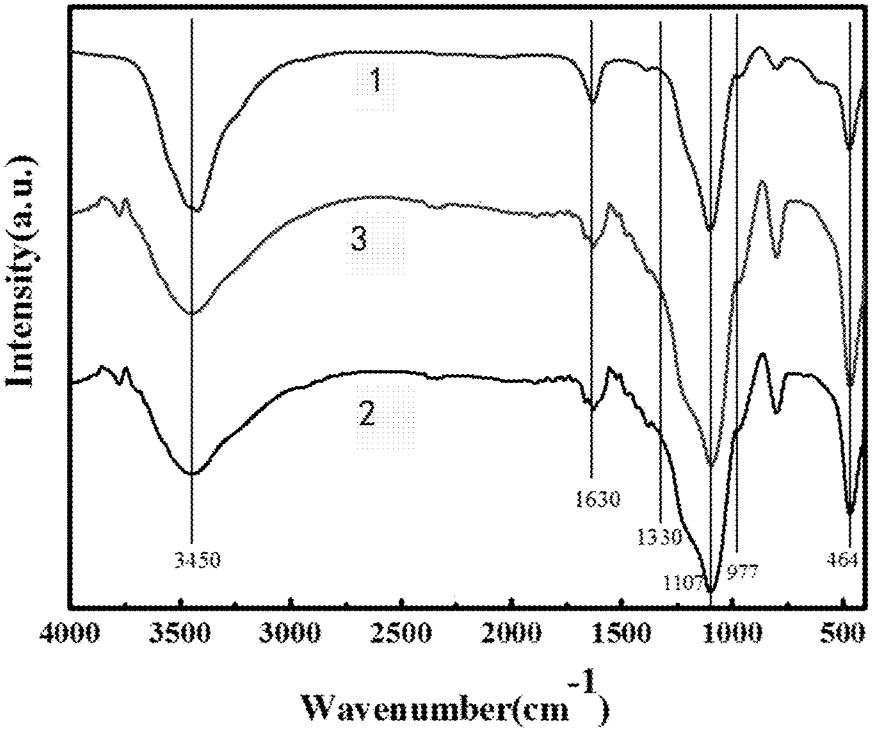
FIG. 13 is a FT-IR spectrum of the phosphorylated inorganic solid metasilicic acid powder of Example 20 and the sulfonated/phosphorylated inorganic solid metasilicic acid powder of Example 21. 1: metasilicic acid powder, 2: phosphorylated metasilicic acid powder, 3: sulfonated/phosphorylated metasilicic acid powder.

In FIG. 13, the peak at 464 $cm^{-1}$ is the bending vibration absorption peak of the Si—O—Si bond, the peak at 1107 $cm^{-1}$ is the absorption vibration peak of the Si—O bond, the peak at 3450 $cm^{-1}$ is the hydroxyl absorption peak. In curves 2 and 3, an O—P—O antisymmetric stretching peak appears at 977 $cm^{-1}$, the absorption peak at 1330 $cm^{-1}$ is broadened, attributable to stretching vibration peaks of P—O bonds and the effect of asymmetric stretching vibration of S═O bond superimposed with an antisymmetric stretching vibration of Si—O—Si bond, this absorption peak is caused by stretching vibration of the P—O groups in the framework of metasilicic acid-phosphoric acid. Whereas in curve 1 (dry metasilicic acid solid powder), these two peaks do not appear. Thus, it is stated that in phosphorylated or sulfonated/phosphorylated metasilicic acid particles, phosphate and sulfonate groups are covalently attached to the metasilicic acid molecule.

In addition, the solid acid catalyst of the present invention can also be used in catalytic cracking reactions and alkylation reactions (of olefins and paraffins) in the oil refinery field. For example, the catalyst is used in the reaction of 2-butene and isobutane to obtain 2, 2, 3-trimethylpentane.

Example 22 (Application Example)

0.5 kg of silicon-based sulfonic acid catalyst (from Example 1), 5 kg of 2-butene and 35 kg of isobutane were added to a high pressure reactor, sealed, maintaining reaction pressure of 1 MPa, reaction temperature of 100° C., and reacted for 4 hours, which showed 84% conversion of 2-butene and 98% selectivity to target product 2, 2, 3-trimethylpentane (alkylated gasoline, C8 product) having high octane number with RON value of 98.

The Example 22 demonstrates that solid acid catalyst can be ideally used in alkylation reactions in oil refinery field.

As comparison, above process was repeated except that 0.65 kg of silicon-based phosphoric acid catalyst (from Example 20) was used instead of 0.5 kg of silicon-based sulfonic acid catalyst (from Example 1). The conversion of 2-butene was 81%, and selectivity to target product was 93%.

Also, as comparison, above process was repeated except that 0.6 kg of silicon-based sulfonic acid/phosphoric acid catalyst (from Example 21) was used instead of 0.5 kg of silicon-based sulfonic acid catalyst (from Example 1). The conversion of 2-butene was 82%, and selectivity to target product was 95%.

The above results illustrate that more amounts of silicon-based phosphoric acid catalyst and silicon-based sulfonic/phosphoric acid catalyst need to be used to achieve conversion and yield close to that of silicon-based sulfonic acid catalyst when used in reactions requiring strong acid as catalyst.

Example 23 (Application Example)

Silicon-Based Phosphoric Acid Catalyst for Preparation of β-Enaminone.

A mixture of acetylacetone (100.11 mg, 1.0 mmol) and cyclohexylamine (92.19 mg, 1.0 mmol) was added to a 500 ml flask to mix, the silicon-based phosphoric acid catalyst of Example 20 (1.2 mg) was added, the mixture was heated with a 50° C. oil bath, while stirring the mixture. The starting material had disappeared by TLC detection, the reaction was stopped, the mixture was diluted by adding 150 ml of dichloromethane in the reaction mixture, filtered and the solids were washed with dichloromethane. The filtrate was subjected to distillation under reduced pressure to remove the solvent. The residue was purified by chromatography column (3:1 petroleum ether/ethyl acetate) to obtain yellow oily liquid and the desired product was 4-cyclohexylamino-pent-3-en-2-one in 96% yield.

$^1$H NMR (400 MHz, $CDCl_3$) δ: 10.98 (br s, 1H, NH), 4.90 (s, 1H, CH), 3.36 (t, J=4.5 Hz, 1H, CH), 1.98 (s, 3H, $CH_3$), 1.93 (s, 3H, $CH_3$), 1.73-1.87 (m, 4H, $CH_2$), 1.21-1.38 (m, 6H, $CH_2$); $^{13}$C NMR (100 MHz, $CDCl_3$) δ: 194.4 (C═O), 161.8 (C), 94.9 (CH), 51.5 (CH), 33.8 ($CH_2$), 28.7 ($CH_2$), 25.3 ($CH_2$), 24.4 ($CH_3$), 18.6 ($CH_3$). MS(ESI)(m/z): 182.3 ($[M+H]^+$).

As comparison, above process was repeated except that equal amount of silicon-based sulfonic acid catalyst (from Example 1) was used. The yield of target product was 92%. This illustrates that silicon-based phosphoric acid is more suitable than silicon-based sulfonic acid for preparation of β-enaminone.

Analysis and Characterization

1. Analysis of the Solid Silicon-Based Sulfonic Acid Catalyst Particles of Example 1:

During drying of the metasilicic acid gel of Example 1, controlling drying temperature and drying time, moisture from the metasilicic acid particles was previously sufficiently removed, baking was then performed to prevent particle cracking during baking, thereby facilitating maintenance of the structure and shape of the catalyst particles after baking. The substrate of the catalyst particles after baking (i.e., silicon-based sulfonic acid) is a silica substrate in amorphous form or in the form of an amorphous-ordered structure mixture.

The FT-IR diagram of metasilicic acid and inorganic solid silicon-based sulfonic acid catalytic material of Example 1 (catalyst for short) was shown in FIG. 1.

As can be seen from FIG. 1, after metasilicic acid has been sulfonated, new infrared characteristic absorption peak appears at 1394 $cm^{-1}$, attributed to stretching vibration of O═S═O. In addition, intensity of infrared characteristic signal peak at 1101 $cm^{-1}$ is also significantly increased due to infrared characteristic absorption peak of O—S—O in sulfonic acid group coinciding with asymmetric stretching vibration signal peak of Si—O—Si of catalyst framework main body.

Figure 2:
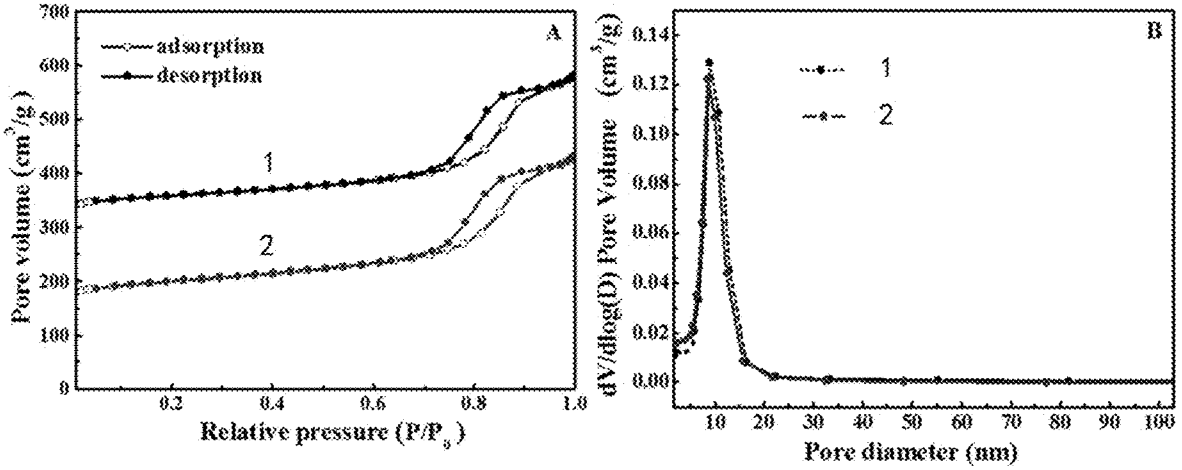
FIG. 2 is the $N_2$ adsorption-desorption diagram (A) and pore size distribution diagram (B) of the inorganic solid silicon-based sulfonic acid catalyst of Example 1 of the present invention. 1: metasilicic acid; 2: silicon-based sulfonic acid.

The $N_2$ adsorption-desorption diagram (A) and pore size distribution diagram (B) of metasilicic acid and inorganic solid silicon-based sulfonic acid catalytic material of Example 1 are shown in FIG. 2.

As can be seen from FIG. 2 (A), according to IUPAC classification, $N_2$ adsorption-desorption isotherms of both metasilicic acid and inorganic solid silicon-based sulfonic acid catalytic material exhibits typical Langmuir type IV isothermal adsorption lines and presence of distinct hysteresis loops of type H1, which are typical characteristics of mesoporous materials. Furthermore, specific surface area and pore structure of metasilicic acid remains substantially unchanged after sulfonation.

Figure 3:
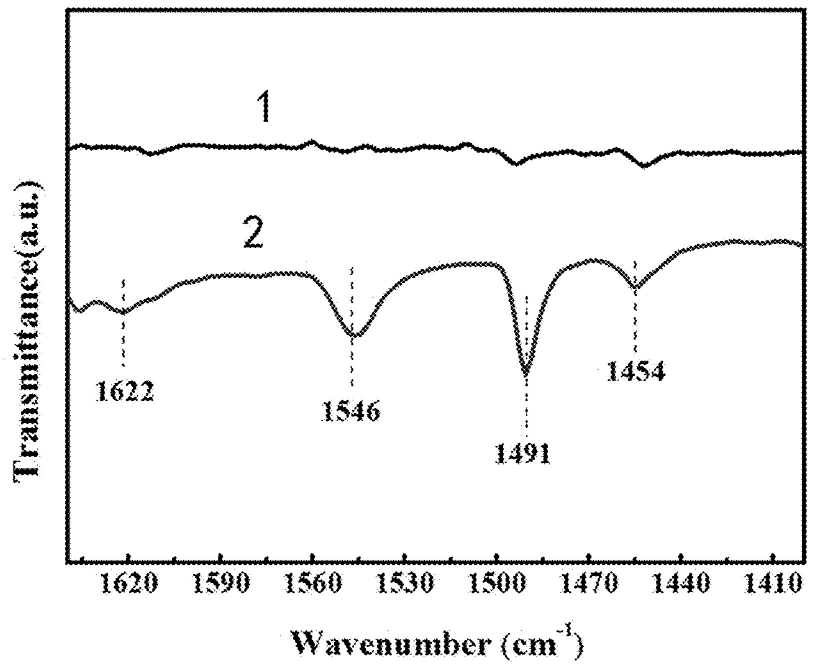
FIG. 3 is a pyridine adsorption infrared spectrogram of the inorganic solid silicon-based sulfonic acid catalyst of Example 1 of the present invention. 1: metasilicic acid; 2: silicon-based sulfonic acid.

Infrared spectra of pyridine adsorption of metasilicic acid and inorganic solid silicon-based sulfonic acid catalytic material of Example 1 are shown in FIG. 3.

As can be seen from FIG. 3, the metasilicic acid sample exhibits no distinct infrared absorption peaks in the wavelength range of 1400 to 1640 $cm^{-1}$. After sulfonation, the inorganic solid silicon-based sulfonic acid catalytic material exhibits four distinct infrared characteristic absorption peaks in the wavelength range of 1400-1640 $cm^{-1}$. Wherein the infrared absorption peaks at 1454 $cm^{-1}$ and 1622 $cm^{-1}$ are the characteristic absorption peaks of pyridine absorbed on Lewis acid centers; the infrared absorption peak at 1546 $cm^{-1}$ is the characteristic absorption peak of pyridine absorbed on the Bronsted acid center, mainly provided by the —$SO_3H$ group; the infrared absorption peak at 1491 $cm^{-1}$ is the characteristic absorption peak resulted from the co-action of pyridines absorbed on both Lewis acid and Bronsted acid centers.

Figure 4:
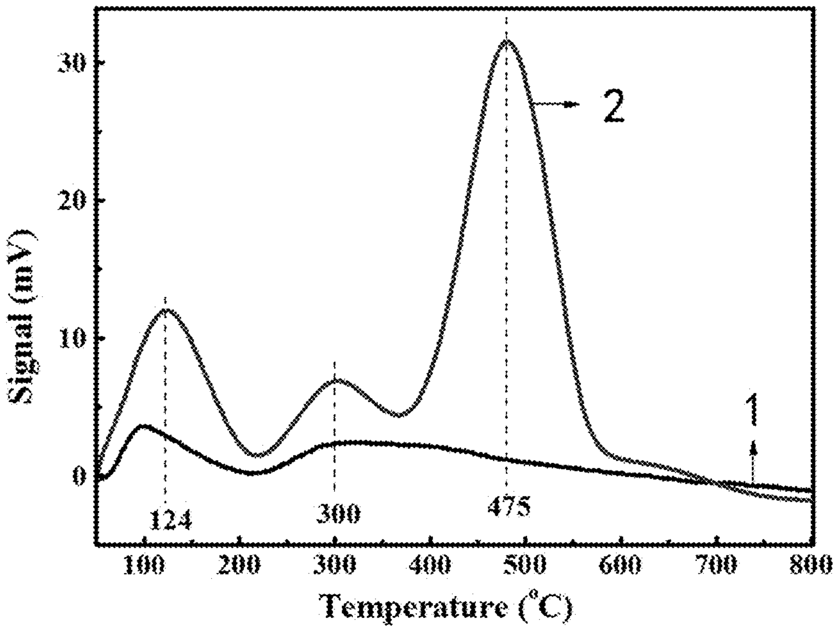
FIG. 4 is the $NH_3$~TPD (ammonia temperature programmed desorption) spectrum of the inorganic solid silicon-based sulfonic acid catalyst of Example 1 of the present invention. 1: metasilicic acid; 2: silicon-based sulfonic acid.

The $NH_3$~TPD spectra of metasilicic acid and inorganic solid silicon-based sulfonic acid catalytic material of Example 1 was shown in FIG. 4.

As can be seen from FIG. 4, TPD curve of inorganic solid silicon-based sulfonic acid catalytic material obtained after sulfonation of metasilicic acid shows three distinct $NH_3$ desorption peaks in range of 50-200° C., 200-400° C. and 400-800° C., corresponding to desorption peaks of $NH_3$ absorbed on weakly acidic sites, moderately strongly acidic sites and strongly acidic sites on its surface, respectively, whereas only small number of weakly acidic sites are present on the surface of metasilicic acid.

Figure 5:
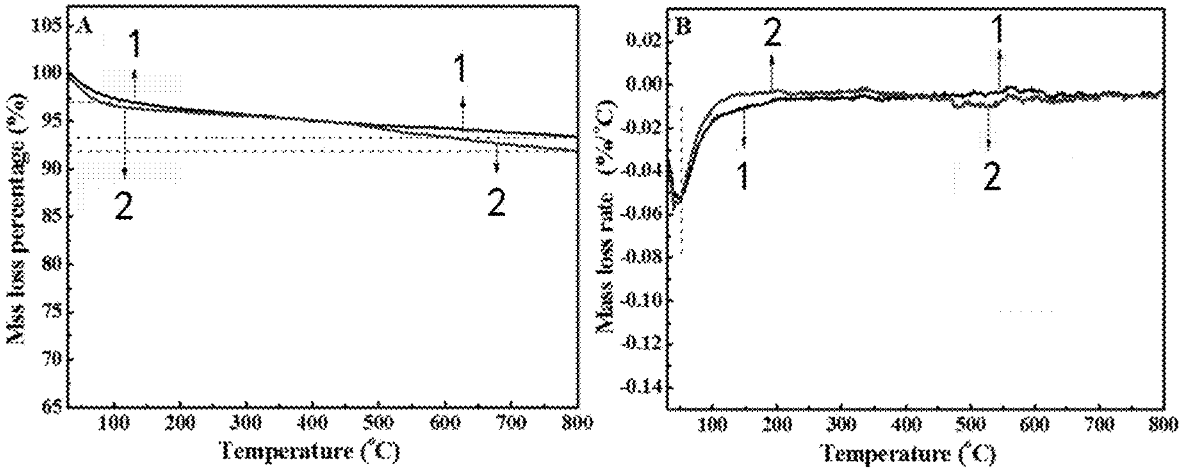
FIG. 5 is a thermogravimetric diagram of the inorganic solid silicon-based sulfonic acid catalyst of Example 1 of the present invention. 1: metasilicic acid; 2: silicon-based sulfonic acid.
Figure 6:
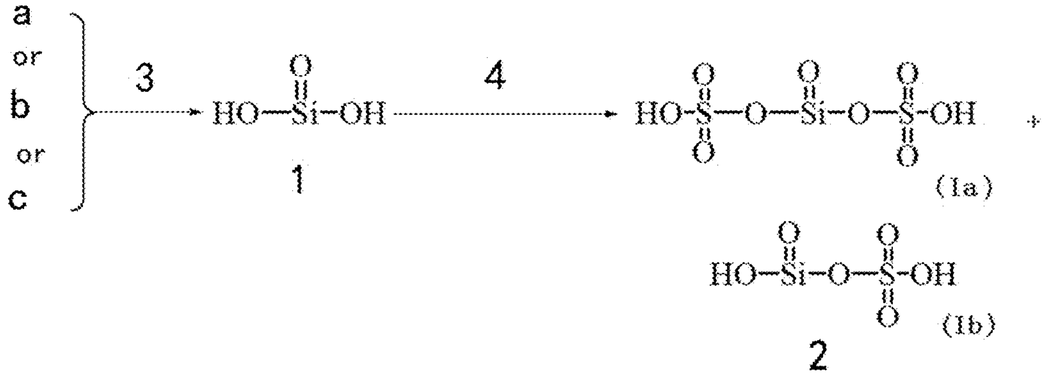
FIG. 6 is a reaction process for preparing silicon-based sulfonic acid. a: silicate salt; b: silicate ester; c: silica gel; 1: metasilicic acid; 2: solid silicon-based sulfonic acid catalyst material; 3: inorganic acid; 4: sulfonating reagent.

The thermogravimetric diagram of metasilicic acid and inorganic solid silicon-based sulfonic acid catalytic material of Example 1 was shown in FIG. 5.

As can be seen in FIG. 5, metasilicic acid shows significant weight loss peak only before 100° C., which is due to desorption of physisorbed water from metasilicic acid surface. After sulfonation of metasilicic acid, there is no significant thermal weight loss, indicating good thermal stability of inorganic solid silicon-based sulfonic acid catalytic material prepared.

As can be seen from the very perfect peaks in FIG. 2, by crystallization of orthosilicic acid gel, the metasilicic acid gel or crystal with improved crystalline structure and pore structure and significantly increased specific surface area are obtained. The metasilicic acid gel or crystal before and after drying as well as the final silicon-based sulfonic acid particles are all mesoporous materials. There is no noticeable difference in structural characteristics of these mesoporous materials, and their pore volume is approximately 0.9 $cm^2/g$ and pore size is approximately 0.87 nm.

In particular, all of these mesoporous materials are resistant to corrosion by strong acids.

Figure 7:
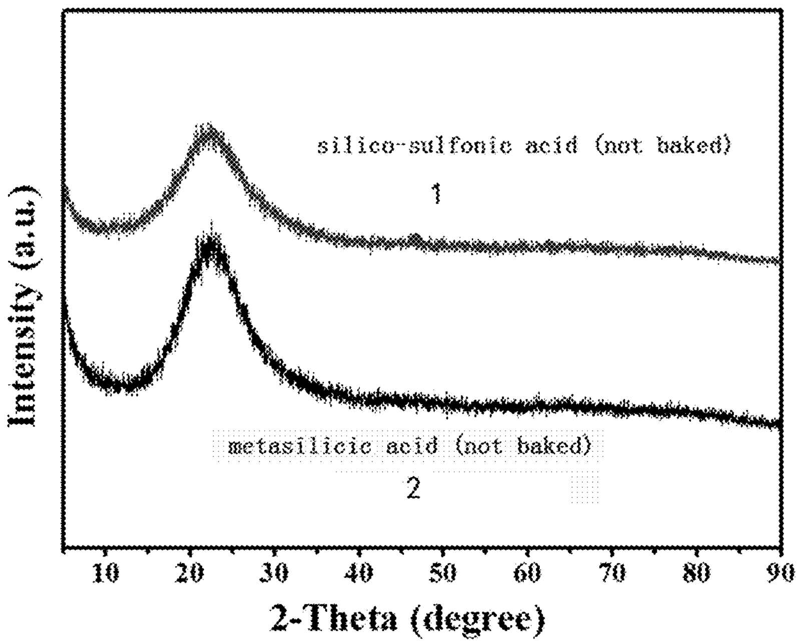
FIG. 7 is a XRD pattern of the dried but unbaked solid acid catalyst of Example 1. 1: silicon-based sulfonic acid powder (unbaked); 2: metasilicic acid powder (unbaked).
Figure 8:
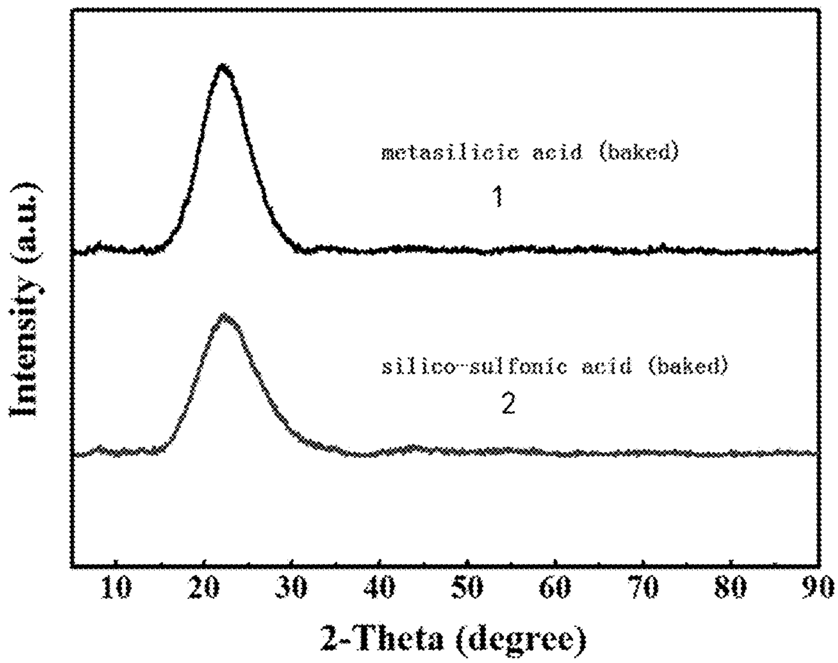
FIG. 8 is a XRD pattern of the baked solid acid catalyst of Example 1. 1: baked metasilicic acid powder; 2: baked silicon-based sulfonic acid powder.

The XRD pattern of the sample was obtained using an X-ray powder diffraction spectroscopy instrument of model D/Max-2550 VB+18 KW of Japan Rigaku. The XRD pattern of the dried and unbaked solid metasilicic acid powder as well as the dried and unbaked solid silicon-based sulfonic acid powder was shown in FIG. 7. The XRD pattern of the dried and baked solid metasilicic acid powder as well as the dried and baked solid silicon-based sulfonic acid powder was shown in FIG. 8. The peak at 22° of 2θAngle represents the characteristic diffraction peaks of metasilicic acid and silicon-sulfonic acid. As can be seen from FIG. 8, the diffraction peaks become visibly smooth after baking, indicating that the strength of the solid acid has increased significantly after the solid acid has been baked, it is also illustrated that the crystallinity of the solid acid after baking is significantly increased, which belongs to silica crystals in amorphous form or short-range ordered arrangement-amorphous mixed form. The substrate of solid acid after baking is not silica gel. In addition, metasilicic acid is sulfonated, the intensity and crystallinity of its diffraction peaks do not substantially change, indicating that the crystalline structure of metasilicic acid is not destroyed during sulfonation.

Figure 9:
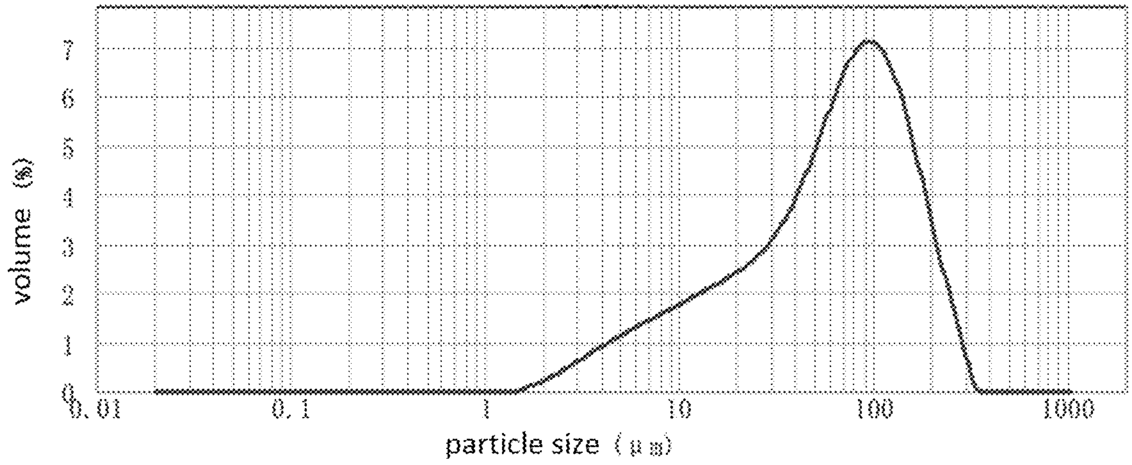
FIGS. 9 and 10 are the particle size distributions of the metasilicic acid and silicon-based sulfonic acid obtained in Example 1, respectively.
Figure 10:
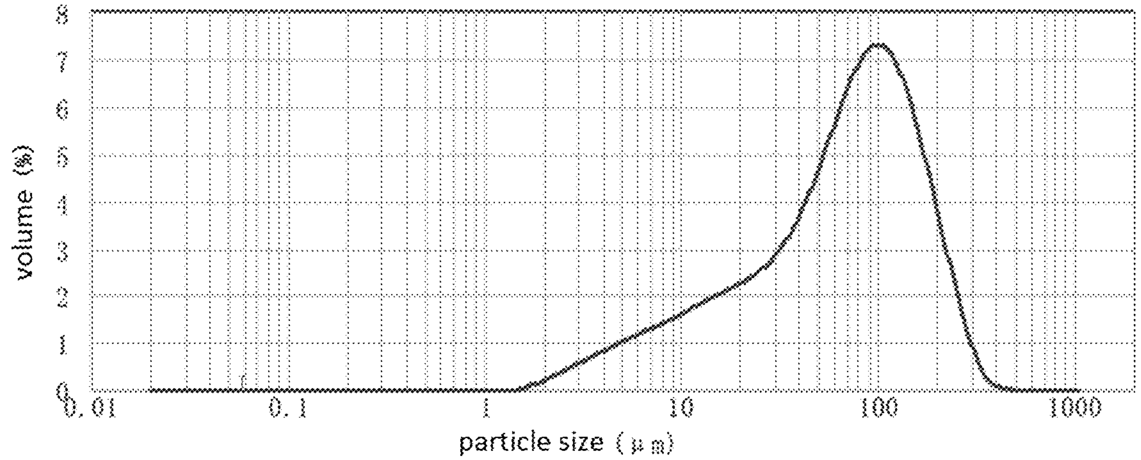

The particle size distributions of metasilicic acid and silicon-based sulfonic acid obtained in Example 1 were determined by using Malvern laser particle sizer as shown in FIGS. 9 and 10. The average particle sizes of both metasilicic acid particles and silicon-based sulfonic acid particles were approximately 95 μm, illustrating that sulfonation reaction did not change size of metasilicic acid particles.

Figure 11:
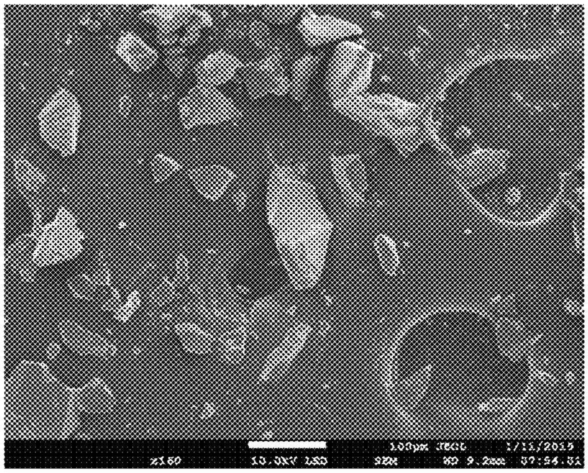
FIG. 11 is a scanning electron microscope (SEM) photograph of the baked inorganic solid silicon-based sulfonic acid particle product of Example 1.

A scanning electron microscopy (SEM) picture of baked inorganic solid silicon-based sulfonic acid particle product of Example 1 was shown in FIG. 11. Wherein silica is commercially available control sample. As can be seen from the SEM picture, average particle size of particles is about 90 μm with better crush strength.

Elemental analysis was performed for catalysts of the examples, wherein content of alkali metals (e.g., sodium and potassium) is below detection limit (below 3 ppm) and content of alkaline earth metals (e.g., calcium and magnesium) is below detection limit.

Figure 12:
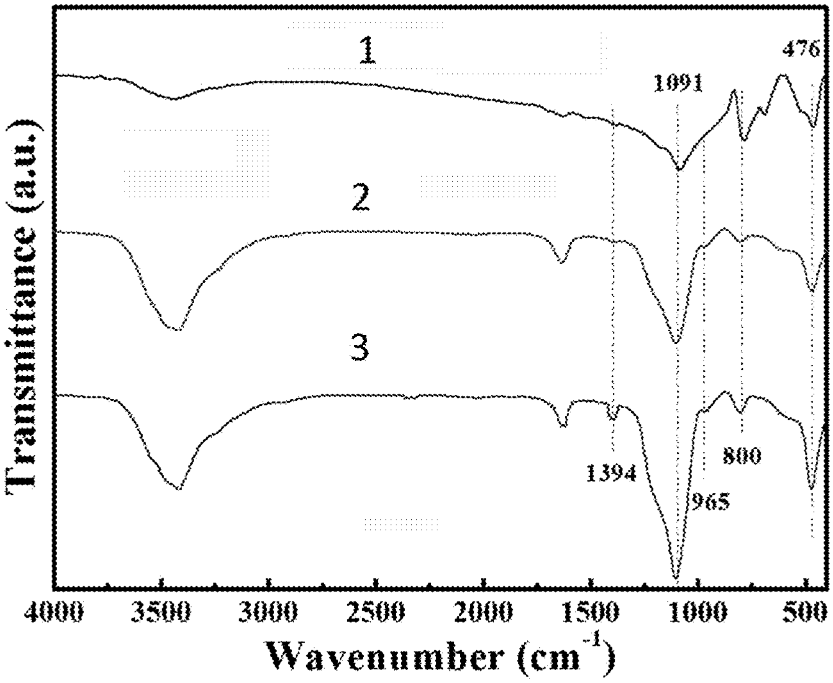
FIG. 12 is a FT-IR spectrum of dried metasilicic acid and baked inorganic solid silicon-based sulfonic acid particles in Example 2. 1: silica powder; 2: metasilicic acid powder; 3: baked silicon-based sulfonic acid powder.

2. FT-IR Analysis of the Silicon-Based Sulfonic Acid Particles of Example 2:

The FT-IR spectra of metasilicic acid and baked inorganic solid silicon-based sulfonic acid particles in Example 2 are shown in FIG. 12.

The symmetric stretching vibration absorption peak of S═O bonds is at 1394 $cm^{-1}$. Flexural vibration absorption peak of Si—O bonds is at 476 $cm^{-1}$. Symmetrical stretching vibration absorption peak of Si—O—Si bonds is at 800 $cm^{-1}$. Absorption peak at 965 $cm^{-1}$ is weak flexural vibration absorption peak of Si—OH bonds (silica does not have this peak). Absorption peak at 1091 $cm^{-1}$ is broadened, which can be attributable to the effect of an asymmetric stretching vibration of the S═O bond superimposed with an antisymmetric stretching vibration of the Si—O—Si bond. The absorption peak at 3421 $cm^{-1}$ is the infrared absorption peak of surface hydroxyl groups. The commercial silica sample has a very weak HO peak, indicating that it adsorbed traces of water from air during storage.

Comparative Example 3

Example I of U.S. Pat. No. 3,929,972 was repeated, except that resulting intermediate product (i.e., particles in form of "sol-gel" soft skin-"sodium metasilicate" hard core) was further dried and baked. The particle size of sodium metasilicate was not disclosed in Example I of the US patent.

1 kg of hard sodium metasilicate pentahydrate (glassy) was crushed and milled. The milling operation appeared very difficult. The resulting granules were divided into two batches, the two batches of granules were sieved with two sieves having mesh sizes of 220 μm and 300 μm, respectively, so as to obtain fine particles of sodium silicate pentahydrate (M1) having a mean particle size of larger than 350 μm and coarse particles of sodium silicate pentahydrate (M2) having a mean particle size of larger than 440 μm, respectively. Weighing 60 g of fine particle raw material and 60 g of coarse particle raw material from fine particles of sodium silicate pentahydrate (M1) and coarse particles of sodium silicate pentahydrate (M2), respectively, then repeating the operations in Example I of U.S. Pat. No. 3,929,972, the sulfonation reaction was carried out at 100° C. using concentrated sulfuric acid (98 wt %) at a molar ratio of sodium metasilicate to sulfuric acid of 1:4. After about 25 minutes of sulfonation, the reaction mixture became a viscous mud that was increasingly difficult to stir, so again added concentrated sulfuric acid at a molar ratio of sodium metasilicate to sulfuric acid of 1:2, the sulfonation reaction was allowed to proceed for 5 hours. The sulfonation reaction mixture (i.e. the granular mixture) was filtered with a sand filter, the filter cake was washed with deionized water until the filtrate was neutral. The obtained white solid powder (wet solid) was dried under vacuum at 110° C. for 5 h, dry inorganic solid silicon-based sulfonic acid powder was obtained. Additional 2 mol of sulfuric acid per mol of sodium metasilicate was then added to the resulting dry powder in order to react further, the resulting reaction mixture was filtered with a sand filter and the filter cake was washed with deionized water until the filtrate was neutral, so as to obtain white granular compounds (T1) and (T2) from fine raw material (M1) and coarse raw material (M2), respectively.

These compounds (T1) and (T2) looked like the mud, the average particle size of compounds (T1) and (T2) was about 27 μm, and about 45 μm, respectively. Since the particle size of the sulfonated compound particles became significantly smaller, illustrating that the sulfonated compound particles formed were not acid resistant, sulfuric acid gradually corroded (i.e. dissolved) the sodium metasilicate particles, the formed silicon-sulfonic acid molecules were detached from the particles into the sulfuric acid solution (liquid phase). Granular compound (T1) or (T2) was rubbed in the palm of the hand, it was felt to be soft with no sandy touch. Clearly, silicon-sulfonic acid molecules were present on the surface of the particulate compound (T1) or (T2) and the structure of the particle (T1) or (T2) was a hard core-soft skin structure, wherein the hard core was sodium metasilicate as the substrate portion of the particle (T1) or (T2) and the soft skin was a relatively soft sol-gel mixture composed of metasilicic acid and silicon-sulfonic acid.

Weighing a sample of 3 g from granular compound (T1), adding into a flask equipped with a stirrer, 20 ml of concentrated sulfuric acid was then added therein and heated to 90° C. with stirring for the sulfonation reaction. As the sulfonation reaction proceeded, the sodium metasilicate hard core gradually became smaller, eventually both the soft skin and the hard core disappeared, and they were broken down by the sulfuric acid into monomolecular silicon-sulfonic acid compounds and tiny particulate silicon-sulfonic acid compounds of nanoscale size.

For comparison, particulate compounds (T1) and (T2) were dried under vacuum at 110° C. for 5 h to obtain dried inorganic solid silicon-sulfonic acid powders (T1A) and (T2A), respectively. Then, dried sulfonated solid powder was baked under nitrogen atmosphere for 3 h at 200° C. to obtain baked powdery silicon-sulfonic acid particles (T1B) and (T2B).

| | T1A (unbaked) | T2A (unbaked) | T1B (baked) | T2B (baked) |
|---|---|---|---|---|
| Mean particle size, μm | 27 | 45 | 27 | 45 |
| BET specific surface area, $m^2/g$ | 87.5 | 85.6 | 89.4 | 86.9 |
| Crush strength (N) | Brittle | Brittle | 55 | 58 |
| Acid amount, mmol/g | Unmeasured | Unmeasured | 0.465 | 0.425 |

Figure 14:
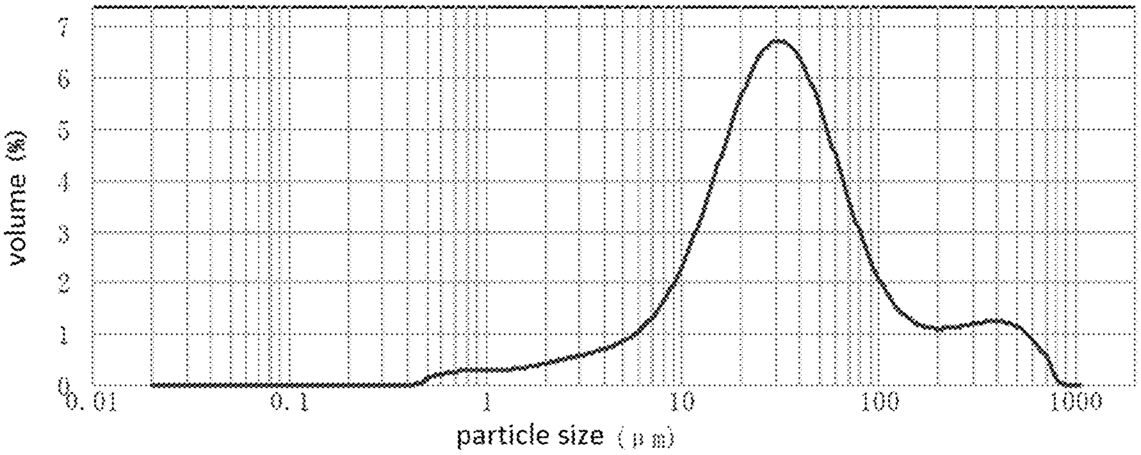
FIG. 14 is the particle size distribution of the powdered silicon-based sulfonic acid particles (T2B) of Comparative Example 3.

The particle size distribution of powdery silicon-sulfonic acid particles (T2B) was measured and results are shown in FIG. 14. As can be seen in FIG. 14, particle size distribution is very broad.

Figure 15:
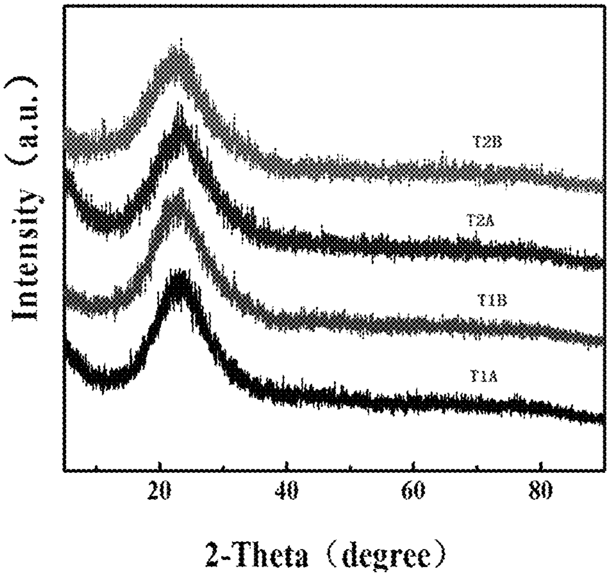
FIG. 15 is a XRD pattern of the solid silicon-based sulfonic acid of Comparative Example 3.

XRD spectroscopy was performed for samples of silicon-sulfonic acid powders (T1A) and (T2A) and silicon-sulfonic acid particles (T1B) and (T2B) and results are shown in FIG. 15. As can be seen from FIG. 15, crystalline structure of silicon-sulfonic acid particles (T1B) and (T2B) was amorphous with low crystallinity and low intensity.

The substrate of sodium metasilicate inside baked particle (T1B or T2B) is alkaline compound and therefore, particles (T1B or T2B) are not acid resistant. When baked particles (T1B or T2B) are used as catalyst in acidic reaction system, which will gradually decompose.

In addition, the above fine particles of sodium silicate pentahydrate (M1) were used, repeating the above preparation process, except that the temperature of the sulfonation reaction is 80° C., 90° C., 110° C. and 120° C., respectively, the acid amounts of the resulting baked silicon-sulfonic acid particulate product were 0.378, 0.402, 0.398 and 0.385 mmol/g, respectively, illustrating that in Example I of U.S. Pat. No. 3,929,972, the optimal sulfonation reaction temperature was approximately 100° C. The acid amounts of the finally obtained particles (T1B) and (T2B) were very low due to detachment of the silicon-sulfonic acid molecules from the sodium metasilicate particles in the sulfonation reaction.

In addition, it is shown according to our experimental results that when Example I of US Patent was repeated using anhydrous sodium metasilicate or sodium metasilicate nonahydrate feedstock instead of sodium metasilicate pentahydrate feedstock, various results obtained were nearly identical to above results.

In addition, as can be seen from claims of US patent, the aim of US patent is to provide monomolecular compound SiO $(HSO_4)_2$ and fine particulate compound of nanoscale size instead of silicon-sulfonic acid particles or powder.

Comparative Example 4

Silica gel sulfonic acid catalytic materials were prepared using silica gel (silica) direct sulfonation method.

Took 200 mL ethyl orthosilicate, 200 mL isopropyl alcohol, 200 mL water, adjusted pH of resulting mixture to 3 with concentrated nitric acid, and 200 mL water was added; the mixture was slowly heated with stirring to 80° C., and then hydrolyzed to pale green gel for 3 h; after aging for 24 h, the mixture is dried at the temperature of 110° C. for 24 h and milled to form silica gel of 90 μm.

5 g of silica gel of 90 μm size was added to 25 mL of chlorosulfonic acid for direct sulfonation, stirred, and sulfonated at 130° C. for 6 h; then, the resulting mixture was cooled to room temperature, filtered, but not washed with deionized water until the filtrate was neutral. The resulting white solid powder was dried under vacuum at 110° C. for 5 h, and finally, inorganic solid silica gel sulfonic acid catalytic material was obtained, the acid amount thereof was measured to be 31.653 mmol/g.

The resulting solid sample after sulfonation was washed with deionized water until the filtrate was neutral, the resulting white solid powder was then dried under vacuum at 110° C. for 5 h, finally, inorganic solid silica gel sulfonic acid catalytic material was obtained with a measured acid amount of only 0.128 mmol/g. This indicates that the silica gel has a strong adsorption to chlorosulfonic acid. If the sulfonated particles were not washed with deionized water, much chlorosulfonic acid would be adsorbed on the surface of the silica gel, resulting in a large increase in the measured acid amount.

The invention claimed is:

1. An inorganic solid silicon-based sulfonic acid and/or phosphoric acid catalyst (h-SSA) in granular form or powder form, comprising:

a substrate component (A): a silicon-containing substrate without sulfonic acid group(s) phosphoric acid group(s); and a silicon-based acid component (B): inorganic silicon-based sulfonic acid and/or phosphoric acid containing sulfonic acid group(s) and/or phosphoric acid group(s);

wherein the substrate component (A) in the above-mentioned silicon-based sulfonic acid and/or phosphoric acid catalyst (h-SSA) includes or is selected from one or two or three of the following silicon-containing substrate components: (1) metasilicic acid; (2) silica gel, and (3) silica;

wherein the inorganic silicon-based sulfonic acid and/or phosphoric acid containing a sulfonic acid group(s) and/or a phosphoric acid group(s) includes one or more selected from a compound of the general formula (I), a compound of the general formula (II) and a compound of the general formula (III):

(I)

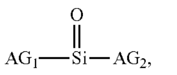

-continued (II)

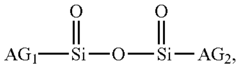

and (III)

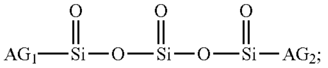

in the above formulae, $-AG_1$ and $-AG_2$ are each independently —O—$SO_3H$, —O—$PO_3H_2$ or —OH, and $-AG_1$ and $-AG_2$ are not both —OH;

wherein the acid amount of the solid acid catalyst (h-SSA) is 0.4-7.0 mmol/g, wherein the acid amount is the amount of acids measured for covalently bonded sulfonic acid groups and phosphoric acid groups in the solid acid catalyst; and wherein the average particle size of the solid acid catalyst (h-SSA) is 15-700 μm.

2. The catalyst according to claim 1, wherein the acid amount of the solid acid catalyst (h-SSA) is 0.6-5.8 mmol/g; and/or the average particle size of the solid acid catalyst (h-SSA) is 30-550 μm.

3. The catalyst according to claim 1, wherein the acid amount of the solid acid catalyst (h-SSA) is 0.8-5.0 mmol/g; and/or the average particle size of the solid acid catalyst (h-SSA) is 40-450 μm.

4. The catalyst according to claim 1, wherein the silicon-based acid component (B) comprises:

60-100 wt % of compounds of general formula (I);

0-40 wt % of compounds of the general formula (II); and 0-30 wt % of compounds of general formula (III);

wherein the weight percent is based on the total weight of the silicon-based acid component (B).

5. The catalyst according to claim 4, wherein the silicon-based acid component (B) comprises:

70-100 wt % of compounds of general formula (I);

0-30 wt % of compounds of the general formula (II); and 0-20 wt % of compounds of general formula (III);

wherein the weight percent is based on the total weight of the silicon-based acid component (B).

6. The catalyst according claim 1, wherein:

the sum of the weights of the compound of the general formula (I), the compound of the general formula (II) and the compound of the general formula (III) is 85-100 wt %, based on the total weight of the silicon-based acid component (B); and/or the sum of the weights of components (A) and (B) is 90-100 wt % of the total weight of the catalyst (h-SSA); and/or the ratio of the weight of the silicon-based acid component (B) to the substrate component (A) is: 0.02-8:1; and/or the average particle size of the solid acid catalyst (h-SSA) is 50-350 μm; and/or the acid amount of the solid acid catalyst (h-SSA) is 1.0-4.8 mmol/g.

7. The catalyst according to claim 1, wherein:

$-AG_1$ and $-AG_2$ are each independently —O—$SO_3H$ and —OH, or —O—$PO_3H_2$ and —OH, and $-AG_1$ and $-AG_2$ are not both —OH; and/or the acid amount of the solid acid catalyst (h-SSA) is 1.0-5.0 mmol/g, and the average particle size of the solid acid catalyst (h-SSA) is 45-400 μm; and/or the sum of the weights of the compound of the general formula (I), the compound of the general formula (II) and the compound of the general formula (III) is 90-100 wt %, based on the total weight of the silicon-based acid component (B); and/or the sum of the weights of components (A) and (B) is 95-100 wt % of the total weight of the catalyst (h-SSA).

8. The catalyst according to claim 1, wherein:

crushing strength of the solid acid catalyst particles (h-SSA) in which the silicon-containing substrate is a silica substrate is in the range of 165-260N; and/or an alkali metal content of the silica substrate in the solid acid catalyst (h-SSA) is 0-300 ppm; and/or the BET specific surface area of the solid acid catalyst (h-SSA) is 50-800 $m^2/g$; and/or the pore volume of the solid acid catalyst (h-SSA) is 50-700 $cm^3/g$; and/or the average pore diameter of the solid acid catalyst (h-SSA) is 4-100 nm; and/or the sum of the weights of the compound of the general formula (I), the compound of the general formula (II) and the compound of the general formula (III) is 95-100 wt %, based on the total weight of the silicon-based acid component (B); and/or the sum of the weights of components (A) and (B) is 98-100 wt % of the total weight of the catalyst (h-SSA).

9. A method for preparing the inorganic solid silicon-based sulfonic acid and/or phosphoric acid catalyst according to claim 1, comprising:

(B) sulfonation and/or phosphorylation of metasilicic acid: reacting a granular metasilicic acid ($H_2SiO_3$) raw material with a sulfonating agent and/or a phosphorylating agent, separating a resulting reaction product and washing with water or with organic solvent, and then drying to obtain dry inorganic solid silicon-based sulfonic acid and/or phosphoric acid particles (h-SSA);

wherein the amount of the sulfonating agent and/or phosphorylating agent relative to metasilicic acid is sufficient so that an acid amount of the dried but unbaked solid acid catalyst (h-SSA) is 0.4-7.0 mmol/g.

10. The method of claim 9, further comprising:

(C) baking: baking the dry granular silicon-based sulfonic acid and/or phosphoric acid solid obtained in step (B) to obtain an inorganic solid silicon-based sulfonic acid and/or phosphoric acid catalyst (h-SSA);

wherein the baking temperature is 120-600° C.

11. The method of claim 10, further comprising:

(A) preparation of granular or powdery metasilicic acid $H_2SiO_3$ raw material: carrying out an ion exchange reaction or a hydrolysis reaction of silicon source and inorganic acid to obtain orthosilicic acid ($H_4SiO_4$) gel or sol; allowing the orthosilicic acid gel or sol to stand for crystallization to obtain a solution containing particulate orthosilicic acid ($H_4SiO_4$) gel, filtering the solution and washing a resulting filter cake with water until a filtrate is neutral, and drying a separated gel to obtain dry granular or powdery metasilicic acid ($H_2SiO_3$) raw material.

12. The method according to claim 11, wherein:

the silicon source in step (A) is one or more of silicate salt, silicate ester and silica gel; and/or the inorganic acid used in step (A) is one or more of hydrochloric acid, sulfuric acid, nitric acid and phosphoric acid; and/or in step (A), the molar ratio of silicon source material and inorganic acid is 0.01-2.0:1; and/or in step (B), the molar ratio of the metasilicic acid to the sulfonating agent and/or phosphorylating agent is 0.01~4.0:1; and/or in step (B), the temperature of the sulfonation reaction is 20° C. to 200° C.; and/or the above step (B) or step (A) is carried out under stirring or under the action of stirring plus ultrasonic waves or microwaves; and/or the baking temperature in step (C) is 200-480° C.

13. A method of preparing the inorganic solid silicon-based sulfonic acid and/or phosphoric acid catalyst according to claim 1, comprising:

allowing a silicon source and an inorganic acid to carry out ion exchange reaction or hydrolysis reaction to obtain orthosilicic acid ($H_4SiO_4$) gel or sol;

standing the orthosilicic acid gel or sol for crystallization to obtain a solution containing granular orthosilicic acid ($H_4SiO_4$) gel, filtering the solution and washing a resulting filter cake with water until a filtrate is neutral, drying a separated gel to obtain a dry granular or powdery metasilicic acid ($H_2SiO_3$) raw material;

then, sulfonating and/or phosphorylating the dried granular or powdery metasilicic acid ($H_2SiO_3$) raw material with a sulfonating agent and/or a phosphorylating agent, filtering a resulting reaction mixture and washing a filter cake with water or organic solvent until a filtrate is neutral, drying an isolated granular sulfonated and/or phosphorylated solid, thereby obtaining a dry inorganic solid silicon-based sulfonic acid and/or phosphoric acid powder; and finally, baking the inorganic solid acid powder to obtain a solid acid catalyst (h-SSA).

14. A process comprising contacting one or more reactants of an isomerization reaction, esterification reaction, alkylation reaction, hydroamination of olefins reaction, condensation reaction, nitration reaction, etherification reaction, amination reaction of alcohol, reaction to prepare β-enaminone, multi-component reaction, oxidation reaction and addition reaction with the inorganic solid silicon-based sulfonic acid or phosphoric acid catalyst of claim 1.

* * * * *